United States Patent [19]

Hartmann et al.

[11] 4,406,889
[45] Sep. 27, 1983

[54] DERIVATIVES OF ALDOHEXOSES, INTERMEDIATES, PROCESSES FOR THEIR MANUFACTURE, PREPARATIONS CONTAINING SUCH COMPOUNDS, AND THEIR USE

[75] Inventors: Albert Hartmann, Grenzach, Fed. Rep. of Germany; Gerhard Baschang, Bettingen, Switzerland; Oskar Wacker, Basel, Switzerland; Jaroslav Stanek, Birsfelden, Switzerland

[73] Assignee: Ciba-Geigy Corporation, Ardsley, N.Y.

[21] Appl. No.: 233,223

[22] Filed: Feb. 10, 1981

[30] Foreign Application Priority Data

Feb. 15, 1980 [CH] Switzerland ............... 1265/80

[51] Int. Cl.³ .................. A61K 37/02; A61K 31/71; C07C 103/52
[52] U.S. Cl. ............... 424/177; 260/112.5 R; 424/114; 424/181; 424/85; 424/180
[58] Field of Search ............ 260/112.5 R; 424/177, 424/88, 181, 114

[56] References Cited

U.S. PATENT DOCUMENTS 4,082,735  4/1978  Jones et al. ............ 260/112.5
4,082,736  4/1978  Jones et al. ............ 260/112.5
4,101,536  7/1978  Yamamura et al. ...... 260/112.5
4,235,771  11/1978 Adam et al. ............ 260/112.5

FOREIGN PATENT DOCUMENTS 14984  3/1980  European Pat. Off.
14159  6/1980  European Pat. Off.
2015534  12/1979  United Kingdom.

Primary Examiner—Blondel Hazel
Attorney, Agent, or Firm—Irving N. Feit

[57] ABSTRACT

Described are derivatives of pyranoses of the formula I, manufacturing processes and intermediates, and their use as medicaments.

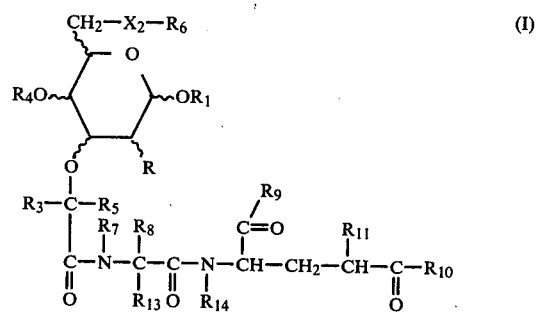

The pyranose moiety in the compounds of the formula I is derived especially from D-glucose, but alternatively from D-galactose or D-mannose.

Characteristic of the compounds of the formula I is the lower alkyl or phenyl-lower alkyl radical $R_8$, which carries an oxycarbonyl, mercaptocarbonyl or aminocarbonyl group, which is bonded to an aliphatic, cycloaliphaticaliphatic, cycloaliphatic or aromatic hydrocarbon radical $R_0$, each of which is optionally substituted and which may be interrupted by oxycarbonyl, mercaptocarbonyl and/or iminocarbonyl and which, like the remaining radicals of the formula I, is defined in patent claim 1.

34 Claims, No Drawings

DERIVATIVES OF ALDOHEXOSES, INTERMEDIATES, PROCESSES FOR THEIR MANUFACTURE, PREPARATIONS CONTAINING SUCH COMPOUNDS, AND THEIR USE

The invention relates to new derivatives of aldohexoses, intermediates and processes for their manufacture, pharmaceutical preparations that contain such compounds, and their use for the manufacture of pharmaceutical preparations or as pharmacologically active compounds.

The invention relates especially to derivatives of pyranoses of the formula (I),

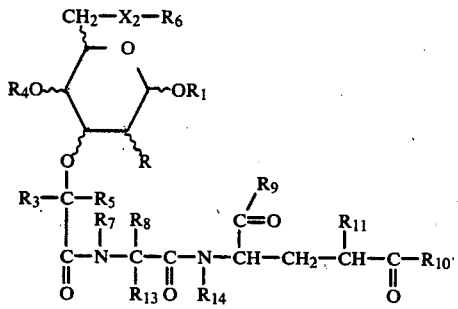

in which

R represents hydroxy, amino or a radical of the formula

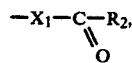

$X_1$ and $X_2$, independently of one another, each represents $NR_{15}$ or an oxygen atom, wherein $R_{15}$ represents hydrogen or lower alkyl, $R_1$ and $R_4$, independently of one another, each represents hydrogen, acyl or a hydroxy-protecting group, $R_6$ represents hydrogen, acyl or, if $X_2$ represents an oxygen atom, a hydroxy-protecting group, $R_2$ represents optionally substituted alkyl, aryl or alkoxy, $R_3$, $R_5$, $R_7$, $R_{13}$ and $R_{14}$, independently of one another, each represents hydrogen or lower alkyl, and $R_8$ represents a lower alkyl or phenyl-lower alkyl radical, which may also be bonded to $R_7$ and which carries an oxycarbonyl, mercaptocarbonyl or aminocarbonyl group which is bonded to an aliphatic, cycloaliphatic-aliphatic, cycloaliphatic or aromatic hydrocarbon radical $R_o$, each of which is optionally substituted and which latter may be interrupted by oxycarbonyl, mercaptocarbonyl and/or iminocarbonyl and must have more than 5 carbon atoms when $R_1$, $R_4$ and $R_6$ represent hydrogen, $R_9$ and $R_{10}$ each represents optionally etherified hydroxy or optionally substituted amino, and $R_{11}$ represents hydrogen or a radical of the formula —C(=O)—$R_{12}$ (Ia), in which $R_{12}$ represents optionally etherified hydroxy or optionally substituted amino, and salts of compounds of the formula I having at least one salt-forming group, processes for the manufacture of compounds of the formula I and of salts of such compounds having salt-forming groups, pharmaceutical preparations containing compounds of the formula I or salts of such compounds having at least one salt-forming group, and the use of compounds of the formula I and of salts of such compounds having salt-forming groups.

Formula I describes derivatives of an aldohexose, especially, for example, D-mannose or D-galactose, but first and foremost D-glucose.

The compounds of the formula (I) may be in the form of pure isomers or mixtures of isomers. For example, the α- or β-configuration may be present at the C-1 of the sugar moiety. In the case of asymmetrical substitution, the configurations are: at the C-$R_3$ especially (D), but in addition alternatively (L), at the C-$R_8$ (D) or (L), but especially (L), and at the CH-$NR_{14}$ especially (D).

There may be mentioned as preferred compounds of the formula (I) those that are derived from D-glucose and have the configuration (D) at the C-$R_3$, the (L)-configuration at the C-$R_8$ and the (D)-configuration at the CH-$NR_{14}$.

Muramyl compounds have at the C-$R_3$ the (D)-configuration, and isomuramyl compounds the (L)-configuration. Muramic acid is 2-amino-2-deoxy-3-O-(1-carboxyethyl)-D-glucose. Normuramic acid is 2-amino-2-deoxy-3-O-carboxymethyl-D-glucose.

In the present context, radicals and compounds referred to as "lower" contain preferably up to and including 7, especially up to and including 4, carbon atoms. Substituted radicals may contain one or more of the same or of different substituents. Radicals for which the number of atoms is not quoted contain no more than 90, especially no more than 30, and preferably fewer than 20, carbon atoms.

The radicals $X_1$ and $X_2$ can have the meanings mentioned but $X_1$ especially represents $NR_{15}$, especially NH, while $X_2$ especially represents an oxygen atom.

An acyl radical $R_1$, $R_4$ or $R_6$ may be formyl, but is preferably optionally substituted hydrocarbylcarbonyl or heterocyclylcarbonyl, hydrocarbyl representing an aliphatic, cycloaliphatic, aromatic, cycloaliphatic-aliphatic or araliphatic hydrocarbon radical and heterocyclyl representing especially a 5- or 6-membered ring having one or more oxygen, nitrogen and/or sulphur atoms as ring members.

An acyl radical $R_1$, $R_4$ or $R_6$ especially represents optionally unsaturated alkanoyl having from 2 to 80, especially from 2 to 25, carbon atoms, or optionally substituted benzoyl, and is, for example, lower alkanoyl, especially acetyl, benzoyl or the acyl radical of a fatty acid, such as stearoyl, oleoyl or palmitoyl, the latter acyl radicals especially being represented by the radical $R_6$. In addition, for example especially the radical $R_6$ may represent the above-mentioned aliphatic, cycloaliphatic or cycloaliphatic-aliphatic radical

defined hereinafter. The following may be mentioned as examples for the last-mentioned radicals $R_6$: N-(D,L-2-hydroxy-myristoyl)-glycyl, N-(cholestan-3(α,β)yl-acetyl)-glycyl, N-cholyl-glycyl, N-(D,L-2-n-hexadecanoylamino-n-hexadecanoyl)-glycyl, N-stearoyl-L-alanyl and 11-stearoylamino-n-undecanoyl.

Hydroxy-protecting groups $R_1$, $R_4$ and/or $R_6$ are, for example, certain acyl radicals, such as lower alkanoyl optionally substituted, for example by halogen, such as 2,2-dichloroacetyl, or acyl radicals of carbonic acid semi-esters, especially tert.-butoxycarbonyl, optionally substituted benzyloxycarbonyl, for example 4-nitrobenzyloxycarbonyl, or diphenylmethoxycarbonyl or 2-halo-lower alkoxycarbonyl, such as 2,2,2-trichloroethoxycarbonyl, also trityl or formyl, or organic silyl or stannyl radicals, also etherifying groups that can readily be split off, such as tert.-lower alkyl, for example tert.-butyl, 2-oxa or 2-thia-aliphatic or -cycloaliphatic hydrocarbon radicals, especially 1-lower alkoxy-lower alkyl or 1-lower alkylthio-lower alkyl, for example methoxymethyl, 1-methoxymethyl, 1-ethoxyethyl, 1-methylthiomethyl, 1-methylthioethyl or 1-ethylthioethyl, or 2-oxa or 2-thiacycloalkyl having from 5 to 7 ring atoms, for example 2-tetrahydrofuryl or 2-tetrahydropyranyl, or corresponding thia-analogues, as well as optionally substituted 1-phenyl-lower alkyl, such as optionally substituted benzyl or diphenylmethyl, there coming into consideration as substituents of the phenyl radicals, for example halogen, such as chlorine, lower alkoxy, such as methoxy, and/or nitro.

The above-mentioned organic silyl or stannyl radicals contain preferably lower alkyl, especially methyl, as substituents of the silicon or tin atoms. Corresponding silyl or stannyl groups are especially tri-lower alkylsilyl, especially trimethylsilyl, and also dimethyl-tert.-butylsilyl, or correspondingly substituted stannyl, for example tri-n-butylstannyl.

As hydroxy-protecting groups $R_4$ and $R_6$ special mention should be given to optionally substituted alkylidene radicals that bond the oxygen atoms in the 4- and 6-position. Alkylidene radicals are especially lower alkylidene, especially methylidene, isopropylidene or propylidene, or alternatively an optionally substituted benzylidene radical. Special mention as hydroxy-protecting group $R_1$ should be given to benzyl.

Preferably, the radicals $R_3$, $R_5$, $R_7$, $R_{13}$ and $R_{14}$ represent hydrogen or methyl.

Chiefly, $R_3$ represents methyl and $R_5$ hydrogen, or $R_3$ and $R_5$ each represent either hydrogen or methyl.

Substituents of substituted alkyl or alkoxy $R_2$ and of substituted aliphatic, cycloaliphatic-aliphatic or cycloaliphatic radicals in $R_8$ are, for example, optionally functionally modified, especially optionally etherified or esterified, hydroxy or mercapto, such as hydroxy, alkoxy, for example lower alkoxy, alkanoyloxy, for example lower alkanoyloxy, or halogen, and mercapto or lower or higher alkylthio, oxo or optionally substituted amino, such as acylamino, for example alkanoylamino.

Optionally substituted aryl $R_2$ or an optionally substituted aromatic hydrocarbon radical in the radical $R_8$ is especially optionally substituted phenyl. Optionally substituted alkoxy $R_2$ is especially phenyl-lower alkoxy. Substituents of phenyl and phenyl-lower alkoxy, it being possible for both the phenyl moiety and the lower alkoxy moiety in the latter to be substituted, are, in a phenyl moiety, for example lower alkyl or optionally functionally modified, especially optionally etherified or esterified, hydroxy, such as hydroxy, lower alkoxy or halogen, and, in a lower alkoxy moiety, for example optionally functionally modified, especially optionally etherified or esterified, hydroxy, such as hydroxy, lower alkoxy, lower alkanoyloxy or halogen.

In the lower alkyl or phenyl-lower alkyl radical $R_8$, the lower alkyl radical is straight-chain or branched. It can also be bonded to $R_7$ and then forms together with the grouping

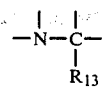

a nitrogen-containing heterocyclic ring, which may contain, for example, 5 and up to and including 7 ring members. The lower alkyl or phenyl-lower alkyl radical $R_8$ and the mentioned heterocyclic ring each carries as substituents an oxycarbonyl

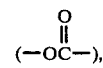

mercaptocarbonyl

or aminocarbonyl

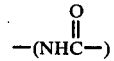

group, there coming into consideration as the linking position both the oxygen, sulphur or nitrogen atom, respectively, and the carbon atom of the carbonyl group. Preferably, the hetero atom is linked to the lower alkyl or phenyl-lower alkyl moiety, whilst the carbon atom of the carbonyl group is bonded to the hydrocarbon radical. At the other side, these substituents are bonded to an optionally substituted aliphatic, cycloaliphatic-aliphatic, cycloaliphatic or aromatic hydrocarbon radical $R_o$, which must be long-chained i.e. have more than 5 carbon atoms when $R_1$, $R_4$ and $R_6$ represent hydrogen. If, on the other hand, $R_1$, $R_4$ and/or $R_6$ for example represent an acyl radical, such as an alkanoyl radical, for example an acetyl radical, the above-mentioned hydrocarbon radical can also have fewer than 5 carbon atoms.

The long-chained aliphatic or cycloaliphatic-aliphatic radical $R_o$ contains, for example, up to and including 90, preferably up to and including 30, carbon atoms. It may be branched or straight-chain, saturated or unsaturated and is then especially an optionally cycloaliphatically substituted alkyl or alkenyl radical. These radicals may carry substituents as mentioned above both in the aliphatic moiety and in the cycloaliphatic moiety. They may also be interrupted by further oxycarbonyl, mercaptocarbonyl or iminocarbonyl groups. In that case the cycloaliphatic radical is positioned preferably directly at one of these separating members. The aliphatic radical lying between the first and the optionally present second separating member is especially a straight or branched alkylene or alkenylene radical having preferably from 1 to 15 carbon atoms.

The cycloaliphatic radical, which can be part of a cycloaliphatic-aliphatic radical, is especially a monocyclic or polycyclic radical, which may optionally be substituted by free, esterified or etherified hydroxy groups, halogen atoms or oxo groups and may be saturated or unsaturated. It contains, for example, up to 24 carbon atoms. It is especially a corresponding mono- or polycyclic cycloalkyl or cycloalkenyl. Polycyclic cycloalkyl or cycloalkenyl is especially tetracyclic, for example cyclopentanopolyhydrophenanthrenyl, which may carry as substituents, for example hydroxy, alkoxy and/or halogen, and have, for example, one or two double bonds.

There may be mentioned as examples of cycloaliphatic-aliphatic radicals derivatives of cholanic acid, such as cholic acid and its derivatives.

An optionally substituted aromatic hydrocarbon radical $R_o$ is especially an optionally substituted phenyl radical, for example phenyl or 4-methylphenyl.

A lower alkyl radical is especially an alkyl radical having from 1 to 7 carbon atoms, which may carry, for example in the 2-position, optionally functionally modified, especially optionally etherified or esterified, hydroxy or mercapto, such as hydroxy, alkoxy, for example lower alkoxy, alkanoyloxy, for example lower alkanoyloxy, or halogen, also mercapto, or alkylthio, such as lower or higher alkylthio, or optionally substituted amino, such as acylamino, for example alkanoylamino.

In the phenyl-lower alkyl radical $R_8$, the lower alkyl radical contains especially from 1 to 3 carbon atoms and is especially methyl.

Etherified hydroxy $R_9$, $R_{10}$ or $R_{12}$ is, for example, hydroxy etherified by an aliphatic radical, such as optionally substituted lower alkoxy, or hydroxy protected by a carboxyl-protecting group, such as benzyloxy or silyloxy, for example trimethylsilyloxy.

Optionally substituted amino $R_9$, $R_{10}$ or $R_{12}$ contains, for example, optionally substituted lower alkyl as substituents, wherein lower alkyl can be substituted, for example, by optionally functionally modified hydroxy, mercapto or carboxy, such as optionally etherified or esterified hydroxy or mercapto, for example hydroxy, lower alkoxy or lower alkylthio, or optionally esterified or amidated carboxy, such as carboxy, lower alkoxycarbonyl or carbamoyl.

In the present context, the above-mentioned general definitions may have the following meanings:

Alkyl represents, inter alia, lower alkyl, for example methyl, ethyl, n-propyl, isopropyl, n-butyl, iso-butyl or tert.-butyl, also n-pentyl, isopentyl, neopentyl, n-hexyl or n-heptyl, or alternatively higher alkyl, such as straight-chain or branched octyl, nonyl, decyl, undecyl, dodecyl, tridecyl, tetradecyl, pentadecyl, hexadecyl, heptadecyl, nonadecyl or henicosyl, as well as higher alkyl radicals of the triacontyl, tetracontyl, pentacontyl, hexacontyl, heptacontyl, octacontyl or nonacontyl series.

Alkenyl is, inter alia, lower alkenyl, for example allyl or methallyl, or higher alkenyl, for example decenyl.

Alkoxy is especially lower alkoxy, for example methoxy, ethoxy, n-propoxy, isopropoxy or n-butoxy.

Phenyl-lower alkoxy is, for example, benzyloxy or 1- or 2-phenylethoxy.

Alkanoyloxy is, inter alia, lower alkanoyloxy, for example acetoxy, propionyloxy or butyryloxy, and also higher alkanoyloxy, for example lauroyloxy, myristinoyloxy, palmitoyloxy, stearoyloxy or behenoyloxy.

Halogen represents, for example, fluorine, chlorine or bromine.

Alkanoylamino is, inter alia, lower alkanoylamino for example acetylamino or propionylamino, and higher alkanoylamino, for example palmitoylamino.

Lower alkylthio is, for example, methylthio or ethylthio whilst higher alkylthio is, for example, tetradecylthio, hexadecylthio or octadecylthio.

Lower alkyl-substituted amino, which may optionally be substituted in the lower alkyl moiety, is, inter alia, lower alkylamino, for example methylamino or ethylamino, carboxy-lower alkylamino, for example carboxymethylamino, or carbamoyl-lower alkylamino.

Lower alkoxycarbonyl is, for example, methoxycarbonyl or ethoxycarbonyl.

Salt-forming groups in the compounds of the formulae I and II are especially optionally present carboxyl groups. Compounds of the formula I having such groups may therefore be in the form of salts, especially pharmaceutically acceptable salts, such as metal, especially alkali metal or alkaline earth metal, salts, for example sodium, potassium, calcium or magnesium salts, or ammonium salts, for example salts with ammonia or organic amines, such as lower alkylamino, for example triethylamine. Compounds of the formulae I and II having a basic group, for example an amino group, can form acid addition salts.

The invention relates especially to peptide derivatives of glucosamine compounds, especially of the formula (Ic)

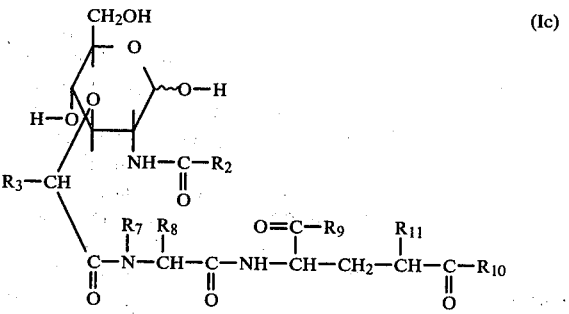

in which $R_2$ represents optionally substituted lower alkyl, phenyl, lower alkoxy or phenyl-lower alkoxy and the remaining radicals have the meanings given above.

The invention relates especially to compounds of the formula Ic in which $R_2$ represents lower alkyl or lower alkoxy each optionally substituted by hydroxy, lower alkoxy, lower alkanoyloxy or halogen, or phenyl or phenyl-lower alkoxy each optionally substituted by lower alkyl, hydroxy, lower alkoxy, lower alkanoyloxy or halogen, $R_3$ represents hydrogen or lower alkyl, $R_7$ represents hydrogen or lower alkyl, and $R_8$ represents a lower alkyl or phenyl-lower alkyl radical which carries as substituent an oxycarbonyl, mercaptocarbonyl or aminocarbonyl group, which is itself in turn bonded to an alkyl or alkenyl radical $R_o$ having more than 6 and up to 90 carbon atoms optionally substituted by hydroxy, lower alkoxy, lower alkanoyloxy, oxo or halogen, or to a cycloaliphatically substituted alkyl or alkenyl radical $R_o$ having, for example, up to 30 carbon atoms, and in which the alkyl, alkenyl and cycloaliphatically substituted alkyl or alkenyl radicals may also be interrupted by one or two oxycarbonyl or iminocarbonyl groups, $R_{11}$ represents hydrogen or a radical of the formula Ia, and each of the radicals $R_9$, $R_{10}$ and $R_{12}$ represents hydroxy, lower alkoxy, amino, or lower alkylamino which is optionally substituted by carboxy, lower alkoxycarbonyl or carbamoyl, wherein in such compounds, for example the radical of the hydroxyacetic acid with the grouping of the formula —CH(R₃)— in which R₃ represents lower alkyl is in the D-form, the radical of the aminoacetic acid with the grouping of the formula —CH(R₈)— is in the L-form, and the radical of the terminal α-aminoglutaric acid compound is in the D-form, and salts, especially pharmaceutically acceptable salts, of such compounds having salt-forming groups.

The invention relates especially to compounds of the formula Ic in which $R_2$ represents lower alkyl having up to 4 carbon atoms, or phenyl, $R_3$ represents hydrogen or lower alkyl having up to 4 carbon atoms, especially methyl, $R_7$ represents hydrogen and $R_8$ represents a lower alkyl radical having from 1 to 4 carbon atoms or a phenyl-lower alkyl radical, each of which carries as substituent an oxycarbonyl, mercaptocarbonyl or aminocarbonyl group which is itself in turn bonded to an alkyl or alkenyl radical $R_o$ having more than 10 and up to 50 carbon atoms optionally substituted by hydroxy, lower alkoxy, oxo or halogen, or to a tetracyclic cycloalkylalkyl radical or cycloalkylalkenyl radical $R_o$ having more than 20 and up to 50 carbon atoms optionally substituted by hydroxy, lower alkoxy, oxo or halogen, wherein such radicals may also be interrupted by 1 or 2 oxycarbonyl or iminocarbonyl groups, $R_9$ represents amino, or lower alkylamino optionally containing carboxy or carbamoyl, $R_{10}$ represents hydroxy and $R_{11}$ represents hydrogen, wherein in such compounds, for example the radical of the hydroxyacetic acid with the grouping of the formula —CH(R₃)— in which $R_3$ represents lower alkyl is in the D-form, the radical of the aminoacetic acid with the grouping of the formula —CH(R₈)— is in the L-form and the radical of the terminal α-aminoglutaric acid compound is in the D-form, and salts, especially pharmaceutically acceptable salts of such compounds having salt-forming groups.

Special mention should be given to compounds of the formula Ic in which $R_2$ represents lower alkyl having up to 4 carbon atoms, especially methyl, and phenyl, $R_3$ represents especially hydrogen, and also lower alkyl having up to 4 carbon atoms, especially methyl, $R_7$ represents hydrogen, $R_8$ represents lower alkyl having from 1 to 4 carbon atoms or benzyl, each of which carries as substituent an oxycarbonyl, mercaptocarbonyl or aminocarbonyl group which is preferably bonded via the hetero atom to the lower alkyl or benzyl radical respectively, and which is itself bonded to alkyl or alkenyl having more than 10 and up to 50 carbon atoms optionally substituted by hydroxy, lower alkoxy or oxo, or to a tetracyclic cycloalkylalkyl or cycloalkenylalkyl radical having more than 20 and up to 50 carbon atoms optionally substituted by hydroxy or lower alkoxy, which radicals may also be interrupted by an oxycarbonyl or iminocarbonyl group, $R_9$ represents amino, $R_{10}$ represents hydroxy and $R_{11}$ represents hydrogen, wherein in such compounds the radical of the hydroxyacetic acid with the grouping of the formula —CH(R₃)— in which $R_3$ represents lower alkyl is in the D-form, the radical of the aminoacetic acid with the grouping of the formula —CH(R₈)— is in the L-form and the radical of the terminal α-aminoglutaric acid compound is in the D-form, and salts, especially pharmaceutically acceptable salts of such compounds having salt-forming groups.

The invention relates first and foremost to the compounds described in the Examples.

The invention relates also to the peptides of the formula II which act as starting materials for the manufacture of the pyranose derivatives of the formula I or are produced as intermediates:

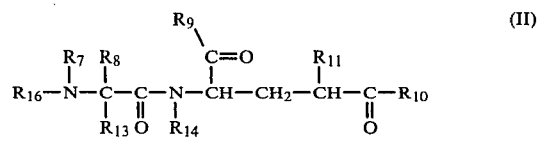

in which $R_{16}$ represents hydrogen or an amino-protecting group, or the radical

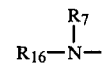

represents an activated amino group, and the remaining substituents have the meanings given above, to pharmaceutical preparations containing the unprotected compounds of the formula II in which $R_{16}$ represents hydrogen, and to their use.

Amino-protecting groups are especially acyl radicals, especially those of carbonic acid semi-derivatives, such as semi-esters, for example lower alkoxycarbonyl optionally substituted by halogen, such as tert.-butoxycarbonyl or 2,2,2-trichloroethoxycarbonyl, or optionally substituted 1-phenyl-lower alkoxycarbonyl, such as benzyloxycarbonyl.

An amino group is activated, for example by reaction with a phosphite.

The new compounds of the formula I can be manufactured in a manner known per se. They are produced, for example by splitting off, in a compound of the formula I in which functional groups are optionally in protected form, at least one group that is readily replaceable by hydrogen, especially a hydroxy-, amino-, carboxy- or mercapto-protecting group, chiefly in the radicals R, $R_1$, $R_4$, $R_6$, $R_9$, $R_{11}$ or $R_{10}$, or by converting at least one functional group into the derivatives corresponding to the end products, for example acylating free hydroxy or amino or esterifying or amidating free carboxy.

Protecting groups of the type mentioned, and the manner in which they are split off, are described, for example in "Protective Groups in Organic Chemistry", Plenum Press, London, New York, 1973, in "The Peptides", volume I, Schröder and Lübke, Academic Press, London, New York, 1965, and in "Methoden der organischen Chemie", Houben-Weyl, 4th edition, vol. 15/1, Georg Thieme Verlag, Stuttgart, 1974.

Thus, carboxyl groups, such as the carboxyl group

are usually protected in esterified form, such ester groupings being readily split under mild conditions. Carboxyl groups protected in this manner contain as esterifying groups especially lower alkyl groups branched in the 1-position or suitably substituted in the 1- or 2-position. Preferred carboxyl groups present in esterified form are, inter alia, tert.-lower alkoxycarbonyl, for example tert.-butoxycarbonyl; arylmethoxycarbonyl having one or two aryl radicals, these representing phenyl radicals optionally mono- or poly-substituted, for example by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example as indicated above, for example 4-nitrobenzyloxycarbonyl or 4-methoxybenzyloxycarbonyl, or diphenylmethoxycarbonyl optionally substituted, for example as indicated above, for example diphenylmethoxycarbonyl or di-(4-methoxyphenyl)-methoxycarbonyl; 1-lower alkoxy-lower alkoxycarbonyl, such as methoxymethoxycarbonyl, 1-methoxyethoxycarbonyl or 1-ethoxymethoxycarbonyl; 1-lower alkylthio-lower alkoxycarbonyl, such as 1-methylthiomethoxycarbonyl or 1-ethylthioethoxycarbonyl; aroylmethoxycarbonyl in which the aroyl group represents benzoyl optionally substituted, for example by halogen, such as bromine, for example phenacyloxycarbonyl; 2-halo-lower alkoxycarbonyl, for example 2,2,2-trichloroethoxycarbonyl, 2-bromoethoxycarbonyl or 2-iodoethoxycarbonyl; or 2-(tri-substituted silyl)-ethoxycarbonyl, in which each of the substituents, independently of one another, represents an aliphatic, araliphatic, cycloaliphatic or aromatic hydrocarbon radical optionally substituted, for example by lower alkyl, lower alkoxy, aryl, halogen and/or by nitro and having, for example, up to 15 carbon atoms, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further protected carboxyl groups present in esterified form are corresponding silyloxycarbonyl groups, especially organic silyloxycarbonyl groups, and also corresponding stannyloxycarbonyl groups. In these groups, the silicon or tin atom preferably contains as substituents lower alkyl, especially methyl, but also lower alkoxy, for example methoxy, and/or halogen, for example chlorine. Suitable silyl or stannyl protecting groups are especially tri-lower alkylsilyl, especially trimethylsilyl, but also dimethyl-tert.-butyl-silyl, lower alkoxy-lower alkyl-halo-silyl, for example methoxymethyl-chloro-silyl or di-lower alkyl-halo-silyl, for example dimethyl-chlorosilyl, or correspondingly substituted stannyl compounds, for example tri-n-butylstannyl.

Preferred protected carboxyl groups are tert.-lower alkoxycarbonyl, such as tert.-butoxycarbonyl, and especially benzyloxycarbonyl optionally substituted, for example as indicated above, such as 4-nitrobenzyloxycarbonyl, or diphenylmethoxycarbonyl.

A protected amino group may be present, for example, in the form of a readily splittable acylamino, arylmethylamino, etherified mercaptoamino, 2-acyl-lower alk-1-en-1-ylamino, silylamino or stannylamino group or in the form of an azido group.

In a corresponding acylamino group, acyl is, for example, the acyl radical of an organic carboxylic acid having, for example, up to 18 carbon atoms, especially of an alkanecarboxylic acid optionally substituted, for example by halogen or aryl, or of a benzoic acid optionally substituted, for example by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example by halogen, lower alkoxy or nitro, for example benzoyl, 4-chlorobenzoyl, 4-methoxybenzoyl or 4-nitrobenzoyl, or lower alkoxycarbonyl branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that preferably represent phenyl optionally mono- or poly-substituted, for example by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group preferably represents benzoyl optionally substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl, in which each of the substituents, independently of one another, represents an aliphatic, araliphatic, cycloaliphatic or aromatic hydrocarbon radical optionally substituted, for example by lower alkyl, lower alkoxy, aryl, halogen or nitro, and having, for example, up to 15 carbon atoms, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethyl-silyl)-ethoxycarbonyl, or 2-triarylsilylethoxycarbonyl, such as 2-triphenylsilylethoxycarbonyl.

Further acyl radicals that come into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, diphenyl-lower alkylphosphoryl optionally substituted, for example by nitro, for example dibenzylphosphoryl or di-4-nitrobenzylphosphoryl, optionally substituted phenoxy-phenyl-phosphonyl, for example phenoxy-phenyl-phosphonyl, di-lower alkylphosphinyl, for example diethylphosphinyl, or optionally substituted diphenylphosphinyl, for example diphenylphosphinyl.

In an arylmethylamino group that represents a mono-, di- or especially tri-arylmethylamino, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl optionally substituted, for example by lower alkyl, such as methyl or tert.-butyl, lower alkoxy, such as methoxy, halogen, such as chlorine, and/or nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, or a benzoic acid optionally substituted, for example by lower alkyl, such as methyl or tert.-butyl, lower alkoxy, such as methoxy, halogen, such as chlorine, and/or nitro, or especially of a carbonic acid semi-ester, such as a carbonic acid lower alkyl semi-ester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en -2-yl.

A silylamino or stannylamino group is especially an organic silylamino or stannylamino group in which the silicon or tin atom contains as substituents preferably lower alkyl, especially methyl, but also lower alkoxy, for example methoxy, and/or halogen, for example chlorine. Corresponding silyl or stannyl groups are especially tri-lower alkylsilyl, especially trimethylsilyl, but also dimethyl-tert.-butyl-silyl, lower alkoxy-lower alkyl-halo-silyl, for example methoxy-methyl-chloro-silyl, or di-lower alkyl-halo-silyl, for example dimethyl-chloro-silyl, or correspondingly substituted stannyl, for example tri-n-butylstannyl.

Preferred amino-protecting groups are acyl radicals of carbonic acid semi-esters, especially tert.-butoxycarbonyl, benzyloxycarbonyl optionally substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl and also trityl or formyl.

A mercapto group can be protected in an analogous manner to a hydroxy group, for example in the manner indicated above for that group.

The splitting off of groups replaceable by hydrogen is carried out by hydrogenolysis or photolysis under mild, usually weakly acidic, but occasionally neutral or weakly basic solvolysis conditions. Silyl groups can also be split off by fluoride ions or compounds yielding fluoride ions.

Certain etherified hydroxy groups, such as tert.-butoxy or tetrahydro-2-pyranyloxy, can be split by solvolysis, especially by treating with an acidic reagent; tert.-butoxy can be split, for example by treating with a strong organic carboxylic acid, such as trifluoroacetic acid, and tetrahydro-2-pyranoyloxy can be split, for example by treating with a mineral acid, such as hydrochloric acid. Others, such as optionally substituted 1-phenyl-lower alkoxy, for example benzyloxy or diphenylmethoxy, can be converted into the free hydroxy group by hydrogenolysis, for example by treating with catalytically activated hydrogen, such as hydrogen in the presence of a noble metal catalysts, for example a palladium catalyst. Acyloxy groups can be split off by solvolysis (for example tert.-butoxycarbonyl or diphenylmethoxycarbonyl can be split off by treating with a strong organic carboxylic acid, such as trifluoroacetic acid), by reduction (for example 2,2,2-trichloroethoxycarbonyl or 2-iodoethoxycarbonyl, usually after formation from the corresponding 2-bromoethoxycarbonyl derivative, can be split off by treating with a reducing metal, such as zinc, in the presence of 90% aqueous acetic acid), or by hydrogenolysis (for example benzyloxycarbonyl or diphenylmethoxycarbonyl can be split off by treating with catalytically activated hydrogen, such as hydrogen in the presence of a noble metal catalyst, for example a palladium or platinum catalyst). Analogously protected mercapto groups can be converted into free mercapto groups in corresponding manner. Acylamino groups used as protected amino groups can be converted into free amino groups in a manner known per se, especially by solvolysis or reduction; tert.-butoxycarbonylamino, for example, can be converted by means of acidolysis (treatment with trifluoroacetic acid), 2,2,2-trichloroethoxycarbonylamino, for example, by means of metallic reduction (treatment with zinc in the presence of acetic acid), and benzyloxycarbonylamino, for example, by means of hydrogenolysis (treatment with hydrogen in the presence of a hydrogenation catalyst). Protected carbonyl groups can be liberated in a variety of ways depending on the nature of the protecting group, which is usually an esterifying group; tert.-butoxycarbonyl or diphenylmethoxycarbonyl can be liberated inter alia by solvolysis, for example by treatment of the corresponding ester compound with a strong organic carboxylic acid, such as trifluoroacetic acid, 2,2,2-trichloroethoxycarbonyl or 2-iodoethoxycarbonyl (usually formed from the corresponding 2-bromoethoxycarbonyl group before splitting, for example by treatment of the corresponding ester compound with a metal iodide, such as sodium iodide) can be liberated by reduction, for example by treatment of the ester compound with a reducing metal, such as zinc in the presence of 90% aqueous acetic acid, and 1-phenyl-lower alkoxycarbonyl, for example benzyloxycarbonyl or diphenylmethoxycarbonyl, can be liberated by hydrogenolysis, for example by treating the ester compound with catalytically activated hydrogen, such as hydrogen in the presence of a noble metal catalyst, such as a palladium or platinum catalyst.

Compounds of the formula I obtainable in accordance with the process can be converted into different compounds of that formula. Thus, for example, a free hydroxy group can be converted into an acyloxy group in a manner known per se, inter alia in the manner described hereinafter, such as by treating with an organic carboxylic acid corresponding to the acyl radical, or preferably with a suitable derivative thereof, such as with an anhydride, including a mixed anhydride, or an activated ester thereof.

Compounds of the formula I having salt-forming groups can be converted into salts in a manner known per se, for example a corresponding compound with a carboxyl group can be converted into a salt by treating with a suitable basic agent, such as an alkali metal or alkaline earth metal hydroxide or carbonate, or with a suitable alkali metal alkoxide.

Isomeric mixtures of compounds of the formula I obtainable in accordance with the process can be separated into the individual isomers in a manner known per se, for example a corresponding racemate of a compound of the formula I having a carboxyl group can be separated by forming a salt with an optically active base, separating the mixture of the diastereoisomeric salts and converting the salt separated off into the free acid.

The new compounds of the formula I can also be manufactured by introducing the radical $R_o$, optionally in stages, by way of the oxycarbonyl, mercaptocarbonyl and/or iminocarbonyl group, in a compound of the formula I in which functional groups are optionally in protected form, in which $R_8$ represents a lower alkyl or phenyl-lower alkyl radical which may also be bonded to $R_7$ and which carries a hydroxy, mercapto, amino or carboxy group optionally present in derivative form, and in which the remaining substituents have the meanings given above, and, if necessary, converting protected functional groups in a resulting compound into the free functional groups and, if desired, converting a compound of the formula I obtainable in accordance with the process into a different compound of the formula I and/or, if desired, converting a salt, obtainable in accordance with the process, of a compound of the formula I having a salt-forming group into the corresponding free compound of the formula I or into a different salt and/or, if desired, converting a compound of the formula I having a salt-forming group obtainable in accordance with the process into a salt and/or, if desired, separating an isomeric mixture of compounds of the formula I obtainable in accordance with the process into the isomeric compounds of the formula I.

The introduction of the radical $R_o$ into such compounds in accordance with the process can be carried out in one step, that is to say the radical can be introduced as a whole, or alternatively, if further oxycarbonyl, mercaptocarbonyl or iminocarbonyl groups are present therein, the introduction can be carried out in stages, first of all the first functional bond and then the remainder being produced in a manner known per se.

This operation is either an acylation reaction, in which a $R_o$—CO— group is introduced into an optionally functionally derivatised hydroxy, mercapto or amino compound, or the esterification or amidation of a carboxylic acid or of a reactive derivative thereof with a compound of the formula $R_o$—OH, $R_o$—SH or $R_o$—NH$_2$ or a reactive functional derivative thereof.

Functional groups in the starting material, which are optionally in protected form, are especially free hydroxy, mercapto or amino groups or free carboxy groups. Suitable protecting groups for these functional groups are especially the hydroxy-, mercapto-, amino- and/or carboxy-protecting groups that can readily be split off, usually used in peptide and/or sugar chemistry, wherein protecting groups that can be split off in the usual manner, for example by solvolysis or reduction, are selected, and these can preferably be split off under neutral or acidic, or optionally under weakly basic conditions. Hydroxy-protecting groups are especially protecting groups that etherify a hydroxy group, such as suitable optionally substituted lower alkyl or phenyl-lower alkyl, especially lower alkyl multi-branched in the 1-position, for example tert.-butyl, or optionally substituted 1-phenyl-lower alkyl, for example benzyl, diphenylmethyl or trityl, and also etherifying groups that together with the oxygen atom of the hydroxy group form an acetal or semi-acetal grouping, especially 2-oxacycloalkyl such as 2-tetrahydrofuranyl or 2-tetrahydropyranyl, but also oxa-lower alkyl bonded by way of a preferably non-terminal carbon atom adjacent to the oxa-oxygen atom, for example 3-oxa-2-n-pentane, as well as optionally substituted alkylidene radicals that bond adjacent oxygen atoms, such as those in the 4- or 6-position. Alkylidene radicals are especially lower alkylidene, especially methylidene, isopropylidene or propylidene, or alternatively an optionally substituted benzylidene radical. Other hydroxy-protecting groups are esterifying protecting groups, such as suitable optionally substituted lower alkoxycarbonyl, especially lower alkoxycarbonyl multi-branched in the α-position to the oxy group or containing halogen in the β-position to the oxy group, for example tert.-butoxycarbonyl, 2,2,2-trichloroethoxycarbonyl, 2-bromoethoxycarbonyl or 2-iodoethoxycarbonyl, or suitable optionally substituted phenyl-lower alkoxycarbonyl, such as 1-phenyl-lower alkoxycarbonyl, for example benzyloxycarbonyl or diphenylmethoxycarbonyl. A mercapto group can be protected analogously to a hydroxy group.

Amino-protecting groups are especially acyl radicals, especially those of carbonic acid semi-derivatives, such as carbonic acid semi-esters, for example lower alkoxycarbonyl optionally substituted by halogen, such as tert.-butoxycarbonyl or 2,2,2-trichloroethoxycarbonyl, or optionally substituted 1-phenyl-lower alkoxycarbonyl, such as benzyloxycarbonyl.

A carboxy group is protected preferably in the form of an esterified carboxy group; there come into consideration as protecting groups for carboxyl groups inter alia suitable optionally substituted lower alkyl, especially lower alkyl multi-branched in the α-position or containing halogen in the β-position, for example tert.-butyl, 2,2,2-trichloroethyl, or 2-bromo- or 2-iodoethyl, or suitable optionally substituted phenyl-lower alkyl, especially 1-phenyl-lower alkyl, such as benzyl or diphenylmethyl.

Starting materials having a derivatised hydroxyl, mercapto or amino group in the radical $R_8$ are corresponding derivatives which can be used in the acylation reaction instead of the free hydroxy, mercapto or amino compounds. These are, for example, O-, S- or N-silyl derivatives, such as O-, S- or N-organosilyl derivatives, for example tri-lower alkylsilyl, especially trimethylsilyl, derivatives.

Other suitable derivatives of the starting materials are those in which the hydroxy or mercapto group is present in the form of a reactive esterified hydroxy or mercapto group; suitable reactive esterified hydroxy groups are hydroxy groups esterified by inorganic acids, such as halogen atoms, for example chlorine, bromine or iodine atoms, or hydroxy groups esterified by strong organic acids, such as corresponding sulphonic acids, for example lower alkylsulphonyloxy, especially methylsulphonyloxy, or arylsulphonyloxy, especially p-methylphenylsulphonyloxy.

The acylation of the optionally derivatised hydroxy, mercapto or amino group in the radical $R_8$ can be carried out in a manner known per se using agents introducing the radical $R_o$—CO. These are especially the corresponding acids or preferably their reactive derivatives, it being possible for functional groups optionally present in these agents, if necessary or desired, to be in protected form.

Protecting groups for hydroxy or mercapto groups optionally present in such acids or derivatives are, for example, the above-mentioned etherifying or esterifying radicals, whilst amino groups may be protected, for example, by protecting groups usually used in peptide chemistry, especially by protecting groups that can readily be split off under neutral or acidic, as well as under weakly basic, conditions, such as by corresponding acyl radicals, especially by those of mono-esterified carbonic acid, or they may be protected in salt form.

Reactive derivatives of these acids are especially reactive activated esters or reactive anhydrides, but also reactive cyclic amides of these acids and their salts, it being possible for functional groups optionally present in such acids to be protected, for example as indicated. Reactive derivatives of such acids can also be formed in situ.

Activated esters of acids of the formula $R_o$—COOH are especially esters unsaturated at the linking carbon atom of the esterifying radical, for example of the vinyl ester type, such as vinyl esters themselves (which can be obtained, for example, by transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method; or 1-lower alkoxyvinyl esters (which can be obtained, for example, by treating the corresponding acid with a lower alkoxyacetylene; ethoxyacetylene method) or esters of the amidino type, such as N,N-disubstituted amidino esters (which can be obtained, for example, by treating the corresponding acid which, when using an acid addition salt, for example the hydrochloride, can alternatively be used in the form of a salt, such as an ammonium salt, for example benzyltrimethylammonium salt, with a suitable N,N'-di-substituted carbodiimide, for example N,N'-di-cyclohexylcarbodiimide; carbodiimide method), or N,N-di-substituted amidino esters (which can be obtained, for example, by treating the corresponding acid with a N,N-di-substituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenyl, 4-methylsulphonylphenol, 2,4,5-trichlorophenol, 2,3,4,5,6-pentachlorophenol or 4-phenyldiazophenol, in the presence of a condensing agent, such as N,N'-dicyclohexylcarbodiimide; activated aryl ester method), cyanomethyl esters (which can be obtained, for example, by treating the corresponding acid with chloroacetonitrile in the presence of a base; cyanomethyl ester method), thioesters, especially phenylthioesters optionally substituted, for example by nitro (which can be obtained, for example, by treating the corresponding acid with thiophenols optionally substituted, for example by nitro, inter alia by way of the anhydride or carbodiimide method; activated thiol ester method), or amino or amido esters (which can be obtained, for example, by treating the corresponding acid with a N-hydroxyamino or N-hydroxyamido compound, respectively, for example N-hydroxypiperidine, N-hydroxysuccinimide, N-hydroxyphthalimide or 1-hydroxybenztriazole, for example according to the anhydride or carbodiimide method; activated N-hydroxy ester method).

Anhydrides of acids of the formula $R_o$—COOH may be symmetrical and preferably mixed anhydrides of these acids, that is to say, for example, anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and treatment thereof with nitrous acid; azide method), anhydrides with carbonic acid semi-derivatives, such as with corresponding esters, for example carbonic acid lower alkyl semi-esters (which can be obtained, for example, by treating the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydride method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkanecarboxylic or phenylalkanecarboxylic acid halide, for example phenylacetic, pivalic or trifluoroacetic acid chloride; mixed carboxylic acid anhydride method) or with organic sulphonic acids (which can be obtained, for example, by treating a salt, such as an alkali metal salt, of the corresponding acid with a suitable organic sulphonic acid halide, such as lower alkanesulphonic or arylsulphonic, for example methanesulphonic or p-toluenesulphonic, acid chloride; mixed sulphonic acid anhydride method), as well as symmetrical anhydrides (which can be obtained, for example, by condensation of the corresponding acid in the presence of a carbodiimide or of 1-diethylaminopropine; symmetrical anhydride method).

Suitable cyclic amides are especially amides with five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treating with acetylacetone; pyrazolide method).

Salts of acids of the formula $R_o$—COOH are especially metal salts, such as alkali metal salts, for example sodium or potassium salts.

There are used to acylate the optionally derivatised hydroxy group especially activated esters, especially amino or amido esters, but also anhydrides, especially mixed anhydrides. Starting materials having a hydroxy group present in reactive esterified form are usually reacted with a salt of one of the acids of the formula $R_o$—COOH.

As mentioned, derivatives of the acids can also be formed in situ. For example, N,N'-di-substituted amidino esters can be formed in situ by reacting a mixture of the starting material and the acid of the formula $R_o$—COOH in the presence of a suitable N,N'-di-substituted carbodiimide, for example N,N'-dicyclohexylcarbodiimide. Further, amino or amido esters can be formed in the presence of the starting material to be acylated by reacting a mixture of the desired acid and the corresponding starting material in the presence of a N,N'-di-substituted carbodiimide, for example N,N'-dicyclohexylcarbodiimide, and of a N-hydroxyamine or N-hydroxyamide, for example N-hydroxysuccinimide, optionally in the presence of a suitable base, for example 4-dimethylaminopyridine.

The acylation reactions can be carried out in a manner known per se, the reaction conditions depending especially on the nature of the acylating agent used, normally in the presence of a suitable solvent or diluent or a mixture thereof and, if necessary, in the pesence of a condensing agent which, for example when using an anhydride as acylating agent, may optionally also be an acid-binding agent, while cooling or heating, for example in a temperature range of from approximately −30° C. to approximately +150° C., in a closed reaction vessel and/or in an inert gas atmosphere, for example a nitrogen atmosphere.

The starting materials used in the above process are known or can be produced in a manner known per se; the acylating agents can be produced, for example, as indicated.

The compounds of the present invention can likewise be manufactured by amidating, optionally in stages, the carboxy group in a compound of the formula IV

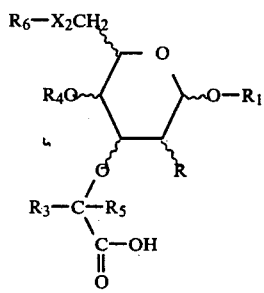

(IV)

in which the substituents have the meanings given above, free functional groups optionally being in protected form, and in which the carboxy group may be in derivative form, with an agent that transfers the radical of the formula

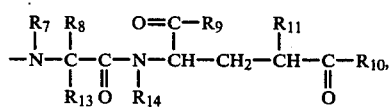

(IVa)

in which the substituents have the meanings given above, functional groups optionally being in protected form, and, if necessary, converting protected functional groups in a resulting compound into free functional groups and, if desired, carrying out additional process steps.

Functional groups in the starting material of the formula IV and in the radical of the formula IVa, which are optionally in protected form, are especially those mentioned above which may be present in protected form in the manner described.

The amidation according to the process of the optionally derivatised carboxy group in a starting material of the formula IV can be carried out in one step or in several steps; i.e. the group of the formula IVa can be introduced as a whole or alternatively in sections, for example by amidation of the optionally derivatised carboxy group in the starting material of the formula IV with an agent yielding a group of the formula

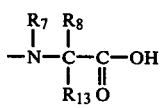

(IVb)

in which the carboxy group may be in functionally modified form and optionally present functional groups may be in protected form, and subsequent amidation of the carboxy group in an intermediate of the formula

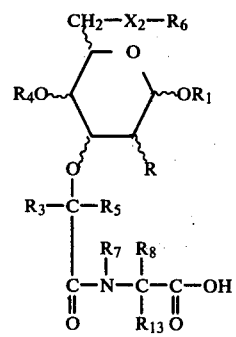

(V)

in which the carboxy group may be in reactive derivative form and optionally present functional groups may be in protected form, with an agent yielding the radical of the formula

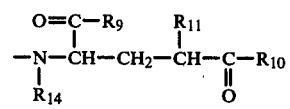

(Va)

in which optionally present functional groups may be in protected form.

The amidation of the optionally derivatised carboxy group in a starting material of the formula IV or in an intermediate or starting material of the formula V can be carried out in a manner known per se, compounds of the formula IV or V, respectively, in which the carboxy group is in reactive derivative form, usually being used as starting materials. The amidating agents used are the dipeptides of the formula

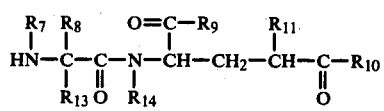

(IVaa)

and amino acids of the formula

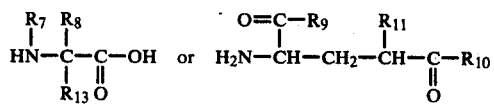

(IVba)            (Vaa)

which correspond to the above radicals of the formulae IVa, IVb and Va respectively and in which functional groups are optionally in protected form and the amino group participating in the amidation reaction may optionally be in reactive derivative form.

Protection of functional groups optionally present in such dipeptides and amino acids, such as the abovementioned hydroxy groups, is preferably provided by means of etherifying and esterifying protecting groups, and amino groups are preferably protected by means of acylating protecting groups, whilst carboxy groups are usually protected in esterified form. Suitable esterifying protecting groups for carboxyl are groups that can readily be split off by solvolysis or reduction, preferably under mild, preferably neutral or acidic, or optionally weakly basic conditions, such as lower alkyl branched at the linking carbon atom and/or containing aryl or aroyl, such as phenyl, biphenylyl or benzoyl, each optionally substituted, for example by halogen, such as chlorine or bromine, by lower alkoxy, for example methoxy, and/or by nitro, for example tert.-butyl, benzyl, diphenylmethyl, 2-biphenylyl-2-propyl or phenacyl, or lower alkyl suitably substituted at the carbon atom adjacent to the linking carbon atom, such as by halogen, for example chlorine, bromine or iodine, or containing an organic silyl group, for example trimethylsilyl, such as 2-halolower alkyl, for example 2,2,2-trichloroethyl, 2-bromoethyl or 2-iodoethyl, or 2-trimethylsilylethyl.

Reactive amino groups present in derivative form in the dipeptides of the formula IVaa and in the amino acids of the formulae IVba and Vaa, are especially silylated amino groups which contain, for example, trimethylsilyl as the derivatising radical.

Reactive derivatives of the starting materials of the formula IV or of the intermediates or starting materials of the formula V are especially reactive activated esters or reactive anhydrides, but also reactive cyclic amides of acids of the formulae IV and V, it also being possible for such reactive derivatives to be formed in situ. Suitable activated esters are, for example, the above-mentioned esters, such as esters unsaturated at the linking carbon atom of the esterifying radical, for example of the vinyl ester type, such as vinyl esters themselves, carbamoylvinyl esters, or 1-lower alkoxyvinyl esters, esters of the amidino type, such as N,N'- or N,N-di-substituted amidino esters, aryl esters, especially phenyl esters suitably substituted by electron-attracting substituents, cyanomethyl esters, thioesters, especially phenylthioesters optionally substituted, for example by nitro, or amino or amido esters. Reactive anhydrides of acids of the formulae IV and V may be symmetrical and preferably mixed anhydrides of these acids, for example the above-mentioned anhydrides with inorganic acids, such as the corresponding acid halides, especially chlorides, azides, anhydrides with carbonic acid semi-derivatives, such as corresponding esters, for example carbonic acid lower alkyl semiesters, or anhydrides with dihalogenated, such as dichlorinated, phosphoric acid, or anhydrides with organic acids, such as mixed anhydrides with organic carboxylic or sulphonic acids, or symmetrical anhydrides. Suitable cyclic amides are, for example, those described above, and are especially amides with five-membered diazacycles of aromatic character, such as amides with imidazoles or pyrazoles.

As mentioned, derivatives of acids of the formulae IV and V can also be formed in situ. Thus, for example, N,N'-di-substituted amidino esters can be formed in situ by reacting a mixture of an acid of the formula IV or V and a dipeptide of the formula IVaa or an amino acid of the formula IVba, or an amino acid of the formula Vaa, respectively, in the presence of a N,N'-di-substituted carbodiimide, for example N,N'-dicyclohexylcarbodiimide. Also, amino or amido esters of an acid of the formula IV or V can be formed in the presence of a dipeptide of the formula IVaa or of an amino acid of the formula IVba, or Vaa, respectively, by reacting a mixture of the desired acid and the corresponding dipeptide compound or the corresponding amino acid compound, respectively, in the presence of a N,N'-di-substituted carbodiimide, for example N,N'-dicyclohexylcarbodiimide, and of a N-hydroxyamine or N-hydroxyamide, for example N-hydroxysuccinimide, optionally in the presence of a suitable base, for example 4-dimethylaminopyridine.

The amidation reactions can be carried out in a manner known per se, the reaction conditions depending chiefly on the nature of the derivative of the acid of the formula IV or V used, usually in the presence of a suitable solvent or diluent or a mixture thereof, and, if necessary, in the presence of a condensing agent which, for example when using an anhydride as derivative of an acid of the formula IV or V, may optionally also be an acid-binding agent, while cooling or heating, for example in a temperature range of from approximately −30° C. to approximately +150° C., in a closed reaction vessel and/or in an inert gas atmosphere, for example a nitrogen atmosphere.

The starting materials used in the above process can be produced in a manner known per se, for example by acylation of the free hydroxy or mercapto group in the radical $R_8$ analogously to the manner described above.

The compounds of the presence invention can likewise be produced by reacting a compound of the formula

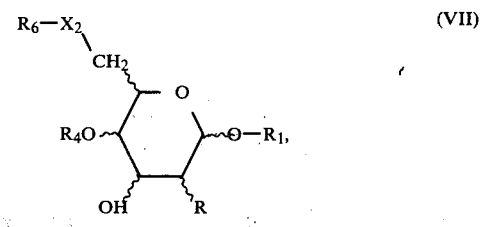

in which the substituents have the meanings given above and functional groups are preferably in protected form, or a reactive derivative thereof, with a compound of the formula

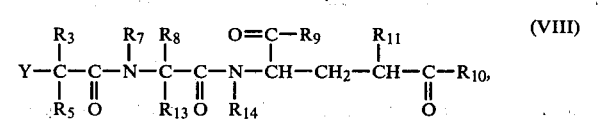

in which Y represents a reactive esterified hydroxy group and the remaining substituents have the meanings given above, functional groups preferably being present in protected form, and, if necessary, converting protected functional groups in a resulting compound into free functional groups and, if desired, optionally carrying out additional process steps.

Functional groups in the starting materials of the formulae VII and VIII, which are optionally in protected form, are especially those mentioned above which may be present in protected form in the manner described.

A reactive derivative of a secondary alcohol of the formula VII used as starting material is especially a corresponding metal, especially alkali metal, for example lithium, sodium or potassium, compound.

A reactive esterified hydroxy group Y is a hydroxy group esterified by a strong acid, such as a corresponding inorganic acid, for example a hydrohalic acid, or by a corresponding organic acid, such as an organic sulphonic acid. The group Y is accordingly especially halogen, especially bromine, but alternatively chlorine or iodine.

The above reaction, in which the starting material of the formula VII is preferably used in the form of a derivative, such as an alkali metal compound, can be carried out in a manner known per se, for example in the presence of a solvent or diluent, such as dimethylformamide, and/or a condensing agent and, if desired or necessary, while cooling or heating, for example in a temperature range of from approximately −30° to approximately +150° C., in a closed reaction vessel and/or in an inert gas atmosphere, for example a nitrogen atmosphere.

The starting materials are known or can be produced in a manner known per se, for example, as described above, by acylation of a free hydroxy, amino or mercapto group in the radical $R_8$ by an acid

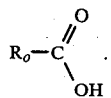

The intermediates of the formula II according to the invention are produced in an analogous manner to that described above, for example, if desired, by splitting off groups readily replaceable by hydrogen, especially in the radicals $R_{16}$, $R_9$, $R_{11}$ or $R_{10}$ or, if desired, by derivatising free functional groups or by binding the amino acids of the formulae (IVba) and (Vaa).

Furthermore, it is also possible to obtain the new compounds of the formula I, provided they are derived from D-glucose, in which $R_2$ is optionally substituted lower alkyl or phenyl, by splitting by means of acid the oxazoline and dioxalane ring in a compound of the formula

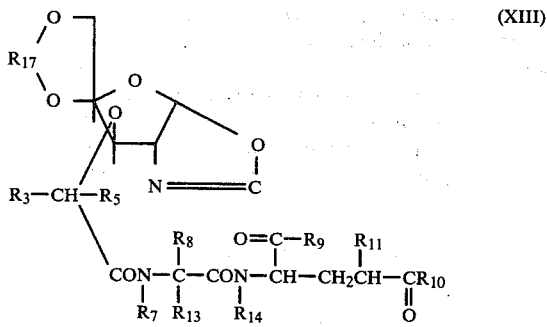

(XIII)

in which $R_{17}$ is an alkylidene or cycloalkylidene group and the remaining substituents have the meanings given above, and splitting off optionally present protecting groups.

Alkylidene is especially lower alkylidene, such as isopropylidene, and cycloalkylidene is especially cyclopentylidene or cyclohexylidene.

This splitting reaction is carried out likewise in a manner known per se, for example with an acidic ion exchanger, especially one with sulphonic acid groups, such as Amberlite IR-120 (a styrene resin with strongly acidic sulpho groups) or Dowex 50 (polystyrenesulphonic acid), or with a strong inorganic or organic acid, such as hydrochloric acid, hydrobromic acid, sulphuric acid or a sulphonic acid, for example methanesulphonic acid, or a phenylsulphonic acid optionally substituted in the aromatic ring, such as p-toluenesulphonic acid or trifluoroacetic acid. If the reaction is carried out in the presence of water, a free hydroxy group is obtained in the 1-position. If, also, one of the carboxyl groups $COR_9$ or $COR_{10}$ and/or $R_{11}$ is esterified by an alcohol, especially a lower alkanol, it can be hydrolysed, especially at elevated temperature, with aqueous acid.

In the resulting compounds, protecting groups on the peptide radical can be split off subsequently, for example by hydrogenolysis, such as, for example, by catalytically activated hydrogen, or by hydrolysis.

The starting materials used in this process can be obtained, for example by introducing the $R_3(R_5)$acetamido-peptide radical in one or more stages into a corresponding oxazoline having a free hydroxy group in the 3-position of the sugar radical.

The new, unprotected lipophilic pyranose derivatives of the formula I, especially the muramyl and normuramyl peptides, and their salts have a number of valuable pharmacological properties, especially a pronounced immunopotentiating action.

Thus, in vivo these compounds considerably increase the ability of mice to form antibodies:

NMRI mice are immunised by intraperitoneal injection of 10 μg of precipitate-free BSA on day 0. 9, 15 and 29 days later, serum samples are taken and examined for their content of anti-BSA antibodies using a passive haemagglutination technique. In the dose used, soluble BSA is subimmunogenic for the recipient animals, that is to say, it is unable to initiate any, or is able to initiate only a very insignificant production of antibodies. Additional treatment of the mice with certain immunopotentiating substances before or after the administration of antigen leads to a rise in the antibody titre in the serum. The effect of the treatment is expressed by the score value achieved, that is to say, by the sum of $\log_2$ titre differences on the three days on which blood samples were taken.

In this test, on intraperitoneal or subcutaneous administration of from 0.5 to 5 mg/kg animal on five successive days after immunisation with BSA, the compounds of the formula (I) are able significantly to increase the antibody production against BSA. In this respect they are greatly superior to the conventional hydrophilic muramyl peptides.

Manifestations of the cell-imparted immunity can also be potentiated in vivo by the mentioned compounds:

Whereas sensitisation of guinea pigs with BSA in incomplete Freund's adjuvant results only in humoral formation of antibodies, the admixture of the lipophilic muramyl peptides according to the invention in a dosage range of from 5 to 50 μg to the antigen-oil emulsion induces delayed hypersensitivity to BSA: three weeks after immunisation, intracutaneous injection of BSA in these animals results in a local inflammation with erythemia and thickening of the skin, which reaches its maximum within 24 to 48 hours. These delayed reactions correspond quantitatively and qualitatively to those that are normally obtained by immunisation with BSA in complete Freund's adjuvant (that is, with the addition of mycobacteria). The $ED_{50}$ values (μg/animal required for the induction of a difference in the reaction volume of 200 μl, (erythemia area x increase in skin thickness) in treated and untreated animals 24 hours after induction) are from 10 to 20 μg.

Deserving of particular emphasis is also the ability of such pyranose derivatives, by administration together with BSA in liposomes (4:1 mixture of egg lecithin and cholesterol or egg lecithin alone; 4 mg/animal) and without the toxic mineral oil component, to induce in guinea pigs a delayed hypersensitivity to BSA. Quantitatively and qualitatively these delayed reactions are likewise identical to those that are obtained by immunisation with BSA in complete Freund's adjuvant. The $ED_{50}$ values are 100 to 300 μg per animal.

Compared with hydrophilic muramyl dipeptides, the new compounds of the formula (I), if they do not contain any protecting groups, exhibit other additional improvements in quality:

Balb/c mice are immunised by intraperitoneal injection of $2 \times 10^4$ P815 mastocytoma cells on day 0. On day 15 the splenocytes of the animals so immunised are examined in vitro for the presence of cytotoxic T-lymphocytes directed against P815 mastocytoma cells. For this purpose, the P815 target cells are labelled with $^{51}$Cr and the extent of the cytotoxic reaction is ascertained by measuring the radioactivity in the culture supernatant. In the dose used, the P815 mastocytoma cells are sub-immunogenic for the recipient mice, that is to say, they induce no, or only a very insignificant, formation of cytotoxic T-cells. Simultaneous intraperitoneal administration of from 1 to 50 µg of the mentioned muramyl peptides of the formula I leads to a significant increase in the formation of cytotoxic T-cells (by a factor of 10 to 30 compared with untreated mice).

The immunopotentiating properties of the unprotected compounds of the formula (I) can also be demonstrated in mice in the case of the induction of specific immunotolerance to transplant antigens by immunisation with autoblasts to which an adjuvant has been added:

In a mixed lymphocyte culture, splenolymphocytes of the prospective transplant recipient (C57 B1/6J mice) are incubated with irradiated splenocytes of the prospective transplant donor (CBA/J mice). T-lymphocytes having specific receptors for the histocompatibility antigens of the donor proliferate and become blast cells; these can be separated from the other cells by sedimentation. The specific blast cells express the relevant idiotypic specificities of the membrane receptors and, admixed with complete Freund's adjuvant (CFA), are injected into the prospective transplant recipients (C57 B1/6J) as auto-immunogens for the induction of specific tolerance to the relevant transplant antigens. The immunisation is carried out four times at intervals of four weeks with autologous anti-CBA/J T-lymphoblasts. Adsorbates of T-autoblasts with the novel compounds of the formula (I) ($10^9$ blast cells are suspended in a solution of 20 mg of substance in 20 ml of PBS; after a two-hour incubation period the cells are centrifuged and washed twice with PBS) are able to induce specific immunotolerance in the absence of CFA, the adsorbates being as effective as the lymphoblasts in CFA.

The unprotected compounds of the formula (I) are also able, in concentrations of from 0.5 to 100 µg/ml in splenocyte cultures of normal mice, to induce the formation of antibody-producing cells (an increase in the 19S-plaque-forming cells by a factor of 10 to 30 above the control value [in the absence of the stimulating substances]): thus in the presence of the mentioned compounds, for example specific antibodies against sheep erythrocytes are formed, without sheep erythrocytes being added to the cultures for the immunisation. On the other hand, when compared with a normally thymus-dependent antigen (sheep erythrocytes), the mentioned substances, in the same concentration range, are also able to increase the immunological reactivity of T-cell-depleted splenocyte cultures (of congenitally athymic nu/nu mice) (by a factor of 10 to 30 compared with untreated control cultures). The mentioned compounds, however, in vitro directly or indirectly induce not only proliferation and synthesis of B-lymphocytes (i.e. of potential antibody-forming cells), but also impart effects to T-lymphocytes (to which regulatory active promotor and suppressor cells and also cytotoxic effector cells belong). Thus, for example, the mentioned compounds in a concentration range of from 1 to 20 µg/ml are able considerably to potentiate (up to 10 times) the reactivity of cortisone-resistant thymus cells compared with allogenic irradiated stimulator lymphocytes.

The above-mentioned effects are probably indirectly brought about owing to the fact that such lipophilic compounds activate macrophages, which in turn promote the reactivity of T- and B-lymphocytes. In fact, it can be shown that the mentioned compounds, even in small concentrations (0.5 to 10 µg/ml), liberate large amounts of "colony stimulating activity" (CSA) from mouse-macrophages (induction of up to 150 to 200 colonies within 7 days from $10^5$ bone marrow cells of mice after the addition of 20% supernatant liquor from macrophage cultures incubated for 24 hours with the substance, compared with 0 to 5 colonies on the addition of supernatant liquors of untreated macrophage cultures). CSA is a biological mediator which is necessary for the differentiation of bone marrow parent cells from macrophages and polymorphonuclear leucocytes. The mentioned compounds in this way cause an increased supply of cells that are of prime importance for nonspecific resistance and for the induction, amplification and expression of specific (lymphocyte-induced) immunoreactions.

The immunopotentiating action of the novel compounds can be demonstrated in vivo: the injection of a muramyl peptide derivative of the formula I according to the invention leads within 3 to 9 hours to a great increase in the CSA concentration in the serum (up to 120 colonies per $10^5$ bone marrow cells of mice after the addition of serum extracted with chloroform [5% final concentration] compared with 0 to 5 colonies in untreated animals). Correspondingly, by administration of the same compounds in vivo the ability of mice to form antibodies is considerably potentiated.

The immunopotentiating properties of the novel compounds of the formula I and their salts can also be demonstrated in tumour models, for example the Ehrlich ascites tumour in the mouse.

The compounds according to the present invention are additionally only slightly toxic: even intraperitoneal administration five times at a dose of 100 mg/kg/day on five successive days was tolerated by the mice apparently without symptoms. Because the doses required for immunostimulation are very small, the therapeutic scope of the novel compounds is very large.

The novel compounds according to the present invention can thus considerably increase the cellular and especially the humoral immunity, both in admixture with the antigen itself (adjuvant effect in the narrower sense) and when administered separately at a different time and at a different site from the antigen injection (systemic immunopotentiation).

The novel compounds according to the present invention may thus be used as adjuvants in admixture with vaccines to improve the success of vaccination and to improve the protection against infection imparted by humoral antibodies and/or cellular immunity against bacterial, viral or parasitic causative organisms.

Finally, the described compounds in admixture with different antigens are suitable as adjuvants in the experimental and industrial manufacture of antisera for therapy and diagnostics and in the induction of immunologically activated lymphocyte populations for cell transfer processes.

Moreover, the novel compounds can also be used, without simultaneous administration of antigens, to promote immune reactions in humans and animals that are already progressing subliminally. The compounds are accordingly particularly suitable for stimulating the body's defence mechanism, for example in the case of chronic and acute infections or in the case of selective (antigen-specific) immunological defects, and in hereditary and also in acquired general (i.e. not antigen-specific) immunological defective conditions, such as occur in old age, in the course of serious primary diseases and especially after therapy with ionising radiation or with hormones having an immunosuppressive action. The mentioned substances can thus be administered preferably also in combinations with antibiotics, chemotherapeutic agents, or other healing means. Finally, the described substances are also suitable for general prophylaxis of infectious diseases in humans and animals.

The protected compounds of the formula I and also the compounds of the formula II are intermediates for the production of compounds of the formula I. In addition, the compounds of the formula II, too, are pharmacologically active.

The invention relates also to the combination of the unprotected pyranose derivatives of the formula I with antibiotics, and this combination causes an increase in the antibiotic activity.

The invention relates also to a process for increasing the antibiotic activity of antibiotics, characterised in that a pyranose derivative of the formula I, especially a muramyl or normuramyl compound, is administered together with an antibiotic. The pyranose derivative can be administered up to 24 hours before or after, but is preferably administered at approximately the same time as, the antibiotic. The combination partners used are especially the muramyl and normuramyl compounds mentioned above as preferred compounds.

The antibiotics are administered in customary manner, such as subcutaneously, intravenously or orally, whereas the muramyl peptides, especially if they are administered separately from the antibiotics, are usually administered subcutaneously.

Of the antibiotics that come into consideration for combination with the pyranose derivatives according to the invention, especially those from the following groups should be mentioned: β-lactam antibiotics, aminoglycosides, tetracyclines, macrolides, lincomycins, polyene antibiotics, polypeptide antibiotics, anthracyclines, chloramphenicols, thiamphenicols, cycloserines, fusidic acids or rifamycins.

As preferred antibiotics from among the β-lactams there may be mentioned the penicillins, cephalosporins, penems, nocardicins, thienamycins and clavulan compounds, for example clavulanic acids.

Penicillin antibiotics are especially amoxycillin, ampicillin, carbenicillin, cloxacillin, cyclacillin, dicloxacillin, mecillinam, methicillin, penicillin, G, penicillin V, pivampicillin, sulbenicillin, azlocillin, ticarcillin, mezlocillin, pivmecillinam or 6-(4-endoazatricyclo[5.2.2.0$^{2,6}$]undec-8-enyl)-methyleneaminopenicillanic acid.

The following from the cephalosporin group may be mentioned, for example cefaclor, cefazaflur, cefazolin, cefadroxil, cefoxitin, cefuroxime, cephacetril, cephalexin, cephaloglycin, cephaloridins, cephalothin, cefamandole, cephanon, cephapirin, cefatrizine, cephradine, cefroxadin (7β-[D-2-amino-2-(1,4-cyclohexadienyl)-acetamido]-3-methoxy-3-cephem-4-carboxylic acid=CGP 9000), cefsulodin, cefotaxime, cefotiam, ceftezole or cefazedone.

Of the nocardicins, for example nocardicin A should be mentioned, and of the thienamycins and clavulanic acids, for example thienamycin and clavulanic acid respectively.

Of the aminoglycosides, special mention should be made of streptomycins, for example streptomycin and streptomycin A, neomycins, for example neomycin B, tobramycins, for example tobramycin or dibekacin, kanamycins, (for example mixtures of kanamycin A, B and C), as well as amicacins, gentamycins (for example mixtures of gentamycin A, $C_1$, $C_2$ and $C_{1a}$) or sisomicins, such as sisomicin or netilmicin, and lividomycin, ribocamycin and paromomycin.

As tetracyclines special mention should be made of tetracycline, doxycycline, chlorotetracycline, oxytetracycline and methacycline.

There should be mentioned as macrolides, for example maridomycin, spiramycins, such as spiramycin I, II and III, erythromycins, for example erythromycin, oleandomycins, for example oleandomycin and tetraacetyloleandomycin, and, as lincomycins, for example lincomycin and clindamycin.

There should be mentioned as polyene antibiotics especially amphothericin B and its methyl ester, or nystatin.

There may be mentioned as polypeptide antibiotics, especially, for example, collistin, gramicidin S, polymyxin B, virginiamycin, tyrothricin, viomycin and vancomycin.

The combination preparations according to the invention have the customary amounts of antibiotics per dosage unit, for example between 50 and 1000 mg, usually between 100 and 500 mg. The amount of pyranose derivative depends on the intended mode of administration. It is higher for orally administered preparations than for injectable preparations. Orally administrable preparations contain from 1 mg up to half the amount of the antibiotics, but usually between 5 and 50 mg, of pyranose derivative of the formula I. When using gastric juice-resistant coated tablets, the dosage can even be less than 1 mg (down to 0.01 mg) of muramyl peptide per tablet. Injectable preparations contain between 10 μg and 50 mg, preferably between 100 μg and 10 mg, of pyranose derivative. These preparations can contain, in addition, the customary amounts of pharmacological carriers, extenders and/or diluents, especially if they are to be used for oral administration. Liposomal forms of administration are also suitable, especially for injectable preparations.

Special mention must be given to pharmaceutical or veterinary medicine preparations, as well as to animal feedstuff and animal feedstuff additives that contain an effective or under-effective dosage of the mentioned antibiotics and, in addition, a muramyl peptide of the formula I.

In the process of the present invention an effective or under-effective dosage of the antibiotic is used, depending on the nature of the latter, for example, from approximately 10 to approximately 1000 mg, especially from approximately 50 to approximately 500 mg per individual dose.

The dosage of the pyranose derivatives of the formula I and their salts depends on the mode of administration and corresponds to the dosage mentioned for the pharmaceutical preparations: the daily dose (oral), for example for warm-blooded animals weighing 70 kg, is between 1 mg and 100 mg.

The high antibiotic activity of the new preparations and of the new process can be demonstrated by "in vivo" tests which are carried out on various species of animal, especially mammals, such as mice. For this purpose, animals are infected with a lethal or sub-lethal dose of a pathogenic micro-organism and then the specified new preparation, or the individual doses of muramyl peptide and antibiotic, are administered. The action is determined as $ED_{50}$, which is that dosage at which 50% of the animals survive.

It has surprisingly now been found that infection with pathogenic germs, especially of the less easily controllable gram-negative bacteria, such as, for example, strains of Aerobacter, Brucella, Escherichia, Klebsiella, Malleomyces, Neisseria, Pasteurella, Proteus, Pseudomonas, Shigella and Vibrio, but also of gram-positive bacteria, such as actinomycetes, clostridia, corynebacteria, diplococci, mycobacteria or staphylococci, or of fungi, such as *Candida albicans, Cryptococcus neoformans, Plastomyces dermatitides* or *Hystoplasma capsulatum*, are inhibited and combated to an increased extent.

The pharmaceutical preparations of the present invention are preferably tablets of gelatin capsules that contain the active substances together with diluents, for example lactose, dextrose, saccharose, mannitol, sorbitol, cellulose and/or glucose and lubricants, for example siliceous earth, talc, stearic acid or salts thereof, such as magnesium or calcium stearate, and/or polyethylene glycol. Tablets also contain binders, for example magnesium aluminium silicate, starches, such as corn, wheat, rice or arrowroot starch, gelatin, tragacanth, methylcellulose, sodium carboxymethylcellulose and/or polyvinylpyrrolidone and, if desired, disintegrators, for example starches, agar, alginic acid or a salt thereof, such as sodium alginate, and/or effervescing mixtures, or adsorbents, colouring substances, flavourings and sweeteners. Injectable preparations are preferably isotonic aqueous solutions or suspensions. Suppositories, ointments or creams are especially fatty emulsions or suspensions. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations which, if desired, may contain other pharmacologically valuable substances, are produced in a manner known per se, for example by means of conventional mixing, granulating or coating processes, and contain from approximately 0.1% to approximately 75%, especially from approximately 1% to approximately 50%, of the specified active substances.

The orally administrable preparations of the present invention may also be provided with a coating that is resistant to gastric juice.

The following Examples illustrate the invention without in any way limiting it.

General: The $R_f$ values quoted were determined on silica gel thin layer plates of the firm Merck. The ratio of eluants to one another in the eluant mixtures used is quoted in parts by volume (V/V). Temperatures are in degrees Centigrade.

EXAMPLE 1

20 ml of a 4.5 normal solution of hydrochloric acid in absolute ethyl acetate are added at room temperature, while stirring and with the exclusion of moisture, to 1.9 g of N-acetyl-1α-O-benzyl-4,6,O-isopropylidenenormuramyl-L-O-[N-behenoyl-glycyl]-seryl-D-isoglutamine-tert-butyl ester dissolved in 20 ml of absolute ethyl acetate. A crystalline product forms after a few minutes and, after stirring for 1 hour, 30 ml of ether are added thereto, the precipitate is filtered with suction, washed and dried over soda-asbestos, yielding 1.6 g; $R_f=0.55$ (chloroform/methanol/water 70:30:5).

1 g (1.05 mmol) of the product obtained above, dissolved in 20 ml of dimethoxyethane/water 20:1, is hydrogenated in the presence of 0.2 g of palladium-on-carbon (10%) for 20 hours at 20° and for 24 hours at 35°. The catalyst is filtered off and washed with the same solvent, and the filtrate, which, according to thin-layer chromatography, contains only by-products, is discarded.

The product (0.53 g) is obtained by intensive extraction of the catalyst with chloroform/ethyl acetate 1:1 and methanol and is further purified by chromatography over silica gel (1:100) in the system chloroform/methanol/water 70:30:5 (3 ml fractions). The material resulting in fractions 66–125, partly in the form of the sodium salt (=from silica gel), is dissolved in water, poured over a strongly acidic ion-exchanger column (Dowex 50, H-form) and eluted first with water and then with dimethoxyethane/water 1:1 (2 ml fractions). The eluates are combined and the dimethoxyethane is evaporated in vacuo. This suspension is brought into solution by the addition of tert.-butanol, is filtered through a millipore filter (Teflon, 0.2μ) and lyophilised.

0.327 g (36%) of N-acetyl-normuramyl-L-(O-[N-behenoyl-glycyl])-seryl-D-isoblutamine in the form of a loose powder remains;

$R_f=0.19$ (chloroform/methanol/water 70:30:5),
$R_f=0.38$ (acetonitrile/water 3:1),
$R_f=0.45$ (ethyl acetate/n-butanol/pyridine/glacial acetic acid/water 42:21:21:6:10).

The starting material used in the present example can be obtained as follows:

2.3 g of N-acetyl-1α-O-benzyl-4,6-O-isopropylidene-normuramyl-L-(O-[N-benzyloxycarbonyl-glycyl])-seryl-D-isoglutamine-tert-butyl ester are dissolved in 50 ml of dimethoxyethane/water 20:1 and, after the addition of 0.5 g of palladium-on-carbon (10%), are treated with hydrogen for 20 minutes. The pH of the solution is maintained at 5 by the addition of 0.1 N HCl (aqueous). The catalyst is filtered off, the reaction solution is concentrated by evaporation and the residue is dried over phosphorus pentoxide.

2 g of the material so obtained are dissolved in 20 ml of pyridine, 0.26 g of N-methylmorpholine is added, and 1.9 g of behenic acid chloride, dissolved in 1 ml of methylene chloride, is added at 0° while stirring.

After stirring for 4 hours at room temperature, the pyridine is evaporated off under reduced pressure, the residue is taken up in 200 ml of ethyl acetate and extracted as follows, using portions of 20 ml each time: twice with water, then twice with sodium bicarbonate solution (0.3%) and finally three more times with water. After drying the mixture over sodium sulphate, the solvent is evaporated and the residue is chromatographed over silica gel (1:50) in the system chloroform/isopropanol 95:5 (15 ml fractions). The appropriate fractions (263-370) are combined and evaporated to dryness and yield 2.0 g of N-acetyl-1α-O-benzyl-4,6-O-isopropylidene-normuramyl-L-O-[N-behenoyl-glycyl]-seryl-D-isoglutamine-tert-butyl ester as a faintly yellowish foam;

$R_f$=0.85 (chloroform/methanol/water 70:30:5),
$R_f$=0.27 (chloroform/isopropanol/glacial acetic acid 70:8:2).

2.5 g (3.7 mmol) of N-acetyl-1α-O-benzyl-4,6-O-isopropylidene-normuramyl-L-seryl-D-isoglutamine-tert-butyl ester, 0.75 g of benzyloxycarbonylglycine, 0.45 g of dimethylaminopyridine and 1.0 g of 1-hydroxybenztriazole are dissolved in 25 ml of dimethylformamide. The solution is cooled to 0°, 0.85 g of dicyclohexylcarbodiimide is added and the whole is stirred for 22 hours at room temperature. The suspension is filtered and the precipitate is washed with ethyl acetate. The combined filtrates are made up to 250 ml by adding further ethyl acetate, are washed 3 times with 20 ml of water each time, 3 times with 20 ml of 2% sodium bicarbonate solution each time and finally 4 times with water. After drying the mixture over sodium sulphate, the solvent is evaporated and the residue is chromatographed over silica gel in a mixture of chloroform/isopropanol 9:1 (10 ml fractions). Fractions 75 to 190 are collected and evaporated to dryness, and, after dissolution in 20 ml of ethyl acetate and adding 20 ml of ether and 100 ml of petroleum ether, the colourless foam is made to crystallise. After filtering with suction and drying in vacuo, there remain 2.7 g (87%) of N-acetyl-1α-O-benzyl-4,6-O-isopropylidene-normuramyl-L-(O-[N-benzyloxycarbonyl-glycyl])-seryl-D-isoglutamine-tert-butyl ester; decomposition point of 104°, $[\alpha]_D^{20}$=+75±1° (c=0.9, ethyl acetate),
$R_f$=0.78 (chloroform/methanol/water 70:30:5),
$R_f$=0.30 (chloroform/isopropanol/glacial acetic acid 70:8:2).

7.0 g (14.35 mmol) of the sodium salt of N-acetyl-1α-O-benzyl-4,6-O-isopropylidene-normuramic acid are suspended in 70 ml of dimethylformamide, and 4.7 g of L-seryl-D-isoglutamine-tert-butyl ester hydrochloride and 4.3 g of N-ethoxycarbonyl-2-ethoxy-1,2-dihydroquinoline are added, and the whole is stirred for 19 hours at room temperature. The mixture is evaporated to dryness, the residue is poured over a silica gel column (1:20), the resulting quinoline is washed down with chloroform and the product is eluted with chloroform/methanol 95:5 in 5 ml fractions. The pure material contained in fractions 35 to 100 is collected. 6.6 g (68%) of N-acetyl-1α-O-benzyl-4,6-O-isopropylidene-normuramyl-L-seryl-D-isoglutamine-tert-butyl ester are obtained as a colourless foam;

$[\alpha]_D^{20}$=81±1° (c=1, methanol).

EXAMPLE 2

2.5 g of N-acetyl-1α-O-benzyl-4,6-O-isopropylidene-normuramyl-L-(O-behenoyl)-seryl-D-isoglutamine-tert-butyl ester are split, analogously to Example 1, with 40 ml of 2 N HCl in ethyl acetate. After stirring for 1 hour at room temperature, the product is precipitated by adding 50 ml of absolute ether and, after stirring for 15 minutes, is filtered in the cold, and the precipitate is dried over soda-asbestos;

$R_f$=0.43 (chloroform/methanol/water 70:30:5).

The slightly impure product is hydrogenated for 65 hours in 25 ml of dimethoxyethane/water 20:1 in the presence of palladium-on-barium sulphate (10%). The catalyst is filtered off and washed, and the combined filtrates are evaporated to dryness (0.8 g). The residue is chromatographed twice over silica gel (1:50) in the system chloroform/methanol 7:3 (5 ml fractions), and the appropriate fractions are combined and evaporated to dryness. The residue is dissolved in dimethoxyethane/water 1:1 and desalted in the usual manner over 10 ml of Dowex 50, H-form. The eluate is concentrated, tert-butanol is added thereto and, after filtration through a millipore filter (Teflon 0.2μ), the mixture is lyophilised. 0.246 g of N-acetyl-normuramyl-L-(O-behenoyl)-seryl-D-isoglutamine is obtained as a colourless powder;

$R_f$=0.23 (chloroform/methanol/water 70:30:5),
$R_f$=0.59 (acetonitrile/water 3:1),
$R_f$=0.39 (ethyl acetate/n-butanol/pyridine/glacial acetic acid/water 42:21:21:6:10).

The starting material is obtained as follows: 1.5 g of N-acetyl-1α-O-benzyl-4,6-O-isopropylidene-normuramyl-L-seryl-D-isoglutamine-tert-butyl ester are dissolved in 15 ml of pyridine, the solution is cooled to 0° and 1.6 g of behenic acid chloride, dissolved in 0.5 ml of dichloromethane, is added. After stirring the mixture for 22 hours at room temperature, the pyridine is distilled off under reduced pressure. The yellowish oil is taken up in 200 ml of ethyl acetate and, in the cold, is washed twice with 15 ml of 1 N citric acid solution each time, twice with 15 ml of water each time, then twice with 5% sodium bicarbonate solution each time and again with water. After drying the mixture over sodium sulphate, the solvent is removed. 2.5 g of N-acetyl-1α-O-benzyl-4,6-O-isopropylidene-normuramyl-L-(O-behenoyl)-seryl-D-isoglutamine-tert-butyl ester are obtained:

$R_f$=0.85 (chloroform/methanol/water 70:30:5),
$R_f$=0.43 (chloroform/isopropanol/glacial acetic acid 70:8:2),
$[\alpha]_D^{20}$=+43° (c=0.611, chloroform).

EXAMPLE 3

A solution of 0.40 g of N-acetyl-1α-O-benzylmuramyl-L-(O-[N-{DL-2-n-hexadecanoylamino-n-hexadecanoyl}-L-alanyl])-threonyl-D-isoglutamine-γ-benzyl ester in 30 ml of dimethylacetamide is treated with hydrogen for 8 days in the presence of 2 g of a palladium-on-barium catalyst (10%). The catalyst is filtered off, the filtrate is evaporated to dryness and the residue is chromatographed over silica gel (1:100) in the system chloroform/methanol 8:2 (2 ml fractions) to remove any dicyclohexylurea still present. The debenzylated material contained in fractions 225-57 is evaporated to dryness. The residue is taken up in doubly distilled water and filtered through a Teflon filter (millipore 0.2μ), and the solution is lyophilised.

N-acetyl-muramyl-L-O-[N-{DL-2-n-hexadecanoylamino-n-hexadecanoyl}-L-alanyl]-threonyl-D-isoglutamine is thus obtained as a loose powder (0.17 g) in the form of the sodium salt;

$[\alpha]_D^{20}$=+1±1° (c=0.5, water),
$R_f$=0.33/0.30 (pair of diastereoisomers, chloroform/methanol/water 70:30:5) and
$R_f$=0.75 (ethyl acetate/n-butanol/pyridine/glacial acetic acid/water 42:21:21:6:10).

The starting material is obtained as follows:

0.185 g of dicyclohexylcarbodiimide is added to a solution of 0.38 g of DL-2-n-hexadecanoylamino-n-hexadecanoic acid and 0.173 g of N-hydroxysuccinimide in a mixture of 5 ml of 1,2-dimethoxyethane, 2 ml of dimethylformamide and 2 ml of chloroform. After stirring for half an hour at room temperature, 0.622 g of N-acetyl-1α-O-benzyl-muramyl-L-(O-L-alanyl)-threonyl-D-isoglutamine-γ-benzyl ester trifluoroacetate and 0.09 ml of N-methylmorpholine are added and the whole is subsequently rinsed with 2 ml of the above-mentioned mixture. After stirring for 23 hours at room temperature, the suspension is diluted with 10 ml of ethyl acetate, is stirred in an ice bath for 30 minutes and filtered. After triturating the filter residue several times with methanol, water and again with methanol, 0.7 g of N-acetyl-1α-O-benzyl-muramyl-L-O-[N-{DL-2-n-hexadecanoylamino-n-hexadecanoyl}-L-alanyl]-threonyl-D-isoglutamine-γ-benzyl ester, still contaminated by dicyclohexylurea, is obtained:

$R_f$=0.35/0.31 (mixture of diastereoisomers, chloroform/methanol 9:1).

1 g of N-acetyl-1α-O-benzyl-4,6-O-isopropylidene-muramyl-L-O-[tert-butoxycarbonyl-L-alanyl]-threonyl-D-isoglutamine-γ-benzyl ester, dissolved in 15 ml of trifluoroacetic acid, is left to stand for 90 minutes at room temperature. The reaction solution is concentrated to a great extent at 25° in a rotary evaporator and the product is precipitated by adding 20 ml of diethyl ether. The supernatant is decanted off, the residue is triturated with fresh ether and decanting is again carried out. After repeating the same operation and drying the residue over soda-asbestos (Merck AG), 0.74 g of N-acetyl-1α-O-benzyl-muramyl-L-(O-L-alanyl)-threonyl-D-isoglutamine-γ-benzyl ester trifluoroacetate is obtained as a colourless powder;

$R_f$=0.40 (chloroform/methanol/water 70:30 5) and
$R_f$=0.52 (ethyl acetate/n-butanol/pyridine/glacial acetic acid/water 42:21:21:6:10).

2.2 g of N-acetyl-1α-O-benzyl-4,6-O-isopropylidene-muramyl-L-threonyl-D-isoglutamine-γ-benzyl ester, 0.57 g of N-BOC-L-alanine, 0.367 g of dimethylaminopyridine and 0.811 g of N-hydroxybenztriazole are dissolved in succession in a mixture of 10 ml of dimethylformamide and 5 ml of dichloromethane. After cooling the solution to 0°, 1.24 g of dicyclohexylcarbodiimide are added and the whole is stirred for 25 hours at room temperature. For working up, the mixture is diluted with ethyl acetate (250 ml), the insoluble dicyclohexylurea is filtered with suction and the filtrate is extracted, using portions of 20 ml in each case (3 times), with water, 0.6 N citric acid solution, saturated sodium bicarbonate solution and again water.

The product obtained after evaporation of the solvent, which, owing to the partial racemisation of L-alanine, is in the form of a mixture of the diastereoisomers, can be separated into its constituents by repeated chromatography over silica gel (1:50) in chloroform/methanol 95:5. The diastereoisomer containing the L-alanine which flows faster in a thin-layer chromatogram, N-acetyl-1α-O-benzyl-4,6-O-isopropylidene-L-(O-[tert-butoxycarbonyl-L-alanyl])-threonyl-D-isoglutamine-γ-benzyl ester, (main fraction 1 g) has an $R_f$ of 0.52, and the isomer containing the D-alanine has an $R_f$ of 0.48 (system: chloroform/methanol 9:1).

8.9 g of the sodium salt of N-acetyl-1α-benzyl-4,6-O-isopropylidene-muramic acid, 6.8 g of L-threonyl-D-isoglutamine-γ-benzyl ester hydrochloride and 4.2 g of N-hydroxysuccinimide are suspended in a mixture of 30 ml of dimethylformamide and 6 ml of dichloromethane. The suspension is cooled to 0°, 4.51 g of dicyclohexylcarbodiimide are added and the whole is stirred for 16 hours at room temperature. The thick suspension is diluted with 50 ml of ethyl acetate, the precipitate is filtered with suction and the filtrate is evaporated to dryness. The resulting residue is taken up in 300 ml of ethyl acetate and, in the cold, is washed in the usual manner with water, 0.6 N citric acid solution, saturated sodium bicarbonate solution and again water.

The oil remaining after evaporation of the solvent is chromatographed over silica gel (1:20) in the system chloroform/methanol 95:5. Fractions 25–47 contain 9.7 g (70% of the theoretical yield) of pure N-acetyl-1α-O-benzyl-4,6-O-isopropylidene-muramyl-L-threonyl-D-isoglutamine-γ-benzyl ester, and a further 10% can be obtained by repeated chromatography of the mixed fraction;

$[\alpha]_D^{20}$ = +92±1° (c=1, methanol),
$R_f$=0.84 (chloroform/methanol/water 75:30:5) and
$R_f$=0.49 (chloroform/methanol 9:1).

9.12 g of N-BOC-L-threonyl-D-isoglutamine-γ-benzyl ester are dissolved in 150 ml of dry ethyl acetate, and the same volume of a 4.5 normal solution of hydrochloric acid in ethyl acetate is added at room temperature, while stirring and with the exclusion of moisture. The separation of the split product, which begins immediately, is completed after 1¼ hours by the addition of 200 ml of diethyl ether. The precipitate is filtered off, washed with ether and dried in vacuo over soda-asbestos (Merck AG). 7.4 g (95% of the theoretical yield) of L-threonyl-D-isoglutamine-γ-benzyl ester hydrochloride are obtained as a colourless powder;

decomposition point 196°–98°,
$[\alpha]_D^{20}$= +13±1° (c=1, methanol),
$R_f$=0.71 (chloroform/methanol/water 70:30:5) and
$R_f$=0.80 (ethyl acetate/n-butanol/pyridine/glacial acetic acid/water 42:21:21:6:10).

The starting material is obtained as follows:

5.48 g of BOC-L-threonine and 6.82 g of D-isoglutamine-γ-benzyl ester hydrochloride are suspended in a mixture of 10 ml of dimethylformamide and 50 ml of ethyl acetate and, after the addition of 2.78 ml of N-methylmorpholine and 6.18 g of 1-ethoxycarbonyl-2-ethoxy-1,2-dihydroquinoline (EEDQ), the whole is stirred for 7 hours at room temperature. The orange-yellow suspension is taken up in 300 ml of ethyl acetate and washed in the usual manner. The neutral substance remaining after evaporation of the solvent is purified by chromatography over silica gel (1:25) in the system chloroform/methanol 95:5. The pure fractions are collected. 10.2 g of N-BOC-L-threonyl-D-isoglutamine-γ-benzyl ester are obtained as a colourless resin;

$[\alpha]_{546\,nm}^{20}$ = −13±1° (c=1, methanol),
$R_f$=0.65 (chloroform/methanol/water 70:30:5) and
$R_f$=0.80 (acetonitrile/water 3:1).

EXAMPLE 4

In a manner analogous to that of the above Examples, the following compounds can be obtained, starting from corresponding starting materials:

N-acetyl-normuramyl-L-(O-[N-{12-hydroxy-cis-9-octadecenoyl}-glycyl])-seryl-D-isoglutamine,
N-benzoyl-normuramyl-L-(O-stearoyl)-seryl-D-isoglutamine,
N-acetyl-muramyl-L-(O-[ω-n-stearoylamino-n-undecanoyl)-threonyl-D-isoglutamine,
N-acetyl-muramyl-L-(O-[N-{3-hydroxy-etiocholenoyl}-6-aminohexanoyl])-γ-hydroxyprolyl-D-isoglutamine,
N-acetyl-muramyl-L-(O-behenoyl)-tyrosyl-D-isoglutamine, N-acetyl-muramyl-L-(S-stearoyl)-cysteinyl-D-isoglutamine, N-acetyl-muramyl-L-([C$_\gamma$]-tetracosylamido-glycyl)-glutamyl-D-isoglutamine, N-acetyl-muramyl-L-[(C$_\gamma$)-lauryl]-glutamyl-D-isoglutamine, N-acetyl-normuramyl-L-($\gamma$-stearoylamino)-$\alpha$-aminobutanoyl-D-isoglutamine.

EXAMPLE 5

1.09 g (3 mmol) of 2-phenyl-4,5-(3-O-carboxymethyl-5,6-O-isopropylidene-D-glucofurano)-$\Delta^2$-oxazoline and 0.35 g of N-hydroxysuccinimide are dissolved in 6 ml of dimethylformamide, the solution is cooled in an ice bath, and 0.74 g (3.6 mmol) of dicyclohexylcarbodiimide is added. After 30 minutes, 0.45 ml of triethylamine is added, and a solution of 1.7 g of L-(O-stearoyl)-seryl-D-glutamic acid dimethyl ester hydrochloride in 10 ml of dimethylformamide is slowly added dropwise while stirring well. The mixture is stirred for a further 0.5 hour while cooling with ice and for 4 hours at room temperature. The reaction product has an R$_f$ of 0.64 and is purified in the following manner:

After concentrating the reaction solution by evaporation in an oil vacuum, the residue is taken up in chloroform, extracted three times by shaking with water and the aqueous phase is extracted with CHCl$_3$. After drying and concentrating the CHCl$_3$ phase by evaporation, the residue is purified by chromatography over silica gel G, Merck (elution with chloroform and CHCl$_3$/acetone 9:1). 1.9 g (72.5% of the theoretical yield) of pure protected muramylpeptide is obtained as an amorphous powder.

1.28 g of this compound is hydrolysed for 17 hours at 40° in a mixture of 20 ml of 0.1 N hydrochloric acid and 40 ml of tetrahydrofuran. The whole is then neutralised with NaHCO$_3$ solution and concentrated by evaporation in vacuo. The residue so obtained is chromatographed over silica gel G, Merck, by successive elution with CHCl$_3$, CHCl$_3$/acetone 9:1, CHCl$_3$/acetone 7:3 and CHCl$_3$/methanol 9:1.

0.54 g, 43.5% of the theoretical yield, of N-benzoyl-normuramyl-L-(O-stearoyl-L-seryl)-D-glutamic acid dimethyl ester having an R$_f$ of 0.65 (CHCl$_3$/methanol 85:15) is obtained. By re-precipitating from ether/petroleum ether, a micro-crystalline powder is obtained having a melting point of 56°-61° and $[\alpha]_D^{20} = +25 \pm 1°$ (c=1, DMSO).

The O-stearoyl-L-seryl-D-glutamic acid dimethyl ester hydrochloride used as starting material is obtained as follows:

5.4 g (2.2 mmol) of 2-ethoxy-N-ethoxycarbonyl-1,2-dihydroquinoline (EEDQ) are added to 4.1 g (2 mmol) of tert-butoxycarbonyl-L-serine, 4.23 g (2 mmol) of D-glutamic acid dimethyl ester hydrochloride and 1.01 g (2 mmol) of N-methylmorpholine in 40 ml of dimethylformamide. After stirring for 16 hours at room temperature, the resulting suspension is filtered and the filtrate is evaporated to dryness. The oily residue is taken up in 150 ml of ethyl acetate and, in the cold, is washed 5 times with 50 ml of 2 N citric acid solution each time, then twice with 50 ml of water each time. The organic phase is dried, concentrated to approximately 40 ml and caused to crystallise by adding, in portions, 150 ml of ether/petroleum ether 2:1. 4.95 g (79%) of tert-butoxycarbonyl-L-seryl-D-glutamic acid dimethyl ester are obtained as colourless needles; m.p. 90°-92°, R$_f$=0.69 (acetonitrile/water 3:1),
R$_f$=0.60 (n-butanol/acetic acid/water 75:75:21).

3.03 g (10 mmol) of stearic acid chloride, dissolved in 30 ml of absolute 1,2-dimethoxyethane, are added dropwise, in the course of 15 minutes, while stirring, to a solution of 3.63 g (10 mmol) of tert-butoxycarbonyl-L-seryl-D-glutamic acid dimethyl ester in 100 ml of absolute pyridine. After leaving the mixture to stand for 30 hours at 4° C., the precipitated pyridine hydrochloride is filtered off, and the filtrate is concentrated by evaporation in a high vacuum and dried (5.9 g).

5.5 g (8.7 mmol) of the wax-like mass are dissolved in 100 ml of absolute ethyl acetate and, while stirring and with the exclusion of moisture, 40 ml of cold 4.5 N HCl in ethyl acetate are added thereto at 0°. After stirring the mixture for 45 minutes, the ethyl acetate phase is extracted 4 times with 50 ml of cold water each time, is dried and, after evaporation of the solvent, is lyophilised from 100 ml of tert-butanol. 4.8 g of O-stearoyl-L-seryl-D-glutamic acid dimethyl ester hydrochloride are obtained as a strongly hygroscopic powder;

$[\alpha]_D^{20} = +11 \pm 1°$ (c=1.2, methanol);
R$_f$=0.46 (n-butanol/acetic acid/water 75:7.5:21),
R$_f$=0.83 (ethyl acetate/n-butanol/pyridine/acetic acid/water 42:21:21:6:10).

EXAMPLE 6

1.45 g (4 mmol) of 2-phenyl-4,5-(3-O-carboxymethyl-5,6-isopropylidene-D-glucofurano-$\Delta^2$-oxazoline, 0.78 g of hydroxybenztriazole, 1.07 g of N-ethyl-N'-(3-dimethylaminooropyl)-carbodiimide hydrochloride and 3 g of L-O-behenoylseryl-D-isoglutamine-$\gamma$-benzyl ester hydrochloride (4.4 mmol) are dissolved in 40 ml of absolute dimethylformamide and the pH is adjusted to 7 with 2.2 ml of triethylamine. After 18 hours at room temperature, the solution is concentrated by evaporation in vacuo to form a syrup, which is taken up in ethyl acetate and extracted by shaking with water, NaHCO$_3$ solution and again with water. The organic phase, dried over Na$_2$SO$_4$, yields, after concentration by evaporation, 2.5 g of a crude product which is purified by chromatography over 80 g of silica gel Merck with CHCl$_3$/methanol 95:5. 1.2 g of the protected muramyl peptide in pure form is obtained as an amorphous substance having an R$_f$ of 0.55.

In order to open up the oxazoline ring and split off the isopropylidene group, 1.1 g of the protected muramyl peptide benzyl ester is hydrolysed in a mixture of 23 ml of tetrahydrofuran and 17 ml of 0.1 N hydrochloric acid for 17 hours at 45°. The reaction solution is then adjusted to pH 6 with NaHCO$_3$ solution and evaporated to dryness in vacuo. The residue is dissolved in CHCl$_3$/ethanol 9:1, and inorganic salts are filtered over a millipore filter, yielding 660 mg, 58% of the theoretical yield, of N-benzoyl-normuramyl-L-(O-behenoyl)-seryl-D-isoglutamine-$\gamma$-benzyl ester as colourless crystals having a decomposition range of 170°-180°;

R$_f$=0.21 (CHCl$_3$/methanol 9:1),
$[\alpha]_D^{20} = +18 \pm 1°$ (c=1, dimethyl sulphoxide).

500 mg of the benzyl ester obtained are hydrogenated with 100 mg of 10% Pd-on-BaSO$_4$ in 10 ml of dimethoxyethane/H$_2$O 9:1. After separating off the catalyst and concentrating the reaction solution by evaporation, 350 mg (77% of the theoretical yield) of N-benzoyl-normuramyl-L-(O-behenoyl)-seryl-D-isoglutamine are obtained as colourless crystals after triturating the residue with warm acetone; decomposition range 166°-172°;

R$_f$=0.18 (CHCl$_3$/methanol 7:1), $[\alpha]_D^{20} = +18 \pm 1°$ (c=1, DMSO).

The L-(O-behenoyl)-seryl-D-isoglutamine-γ-benzyl ester hydrochloride used as starting material is prepared as follows:

16.4 g (80 mmol) of N-tert-butoxycarbonyl-L-serine, 21.81 g (80 mmol) of D-isoglutamine-γ-benzyl ester hydrochloride, 8.9 ml (80 mmol) of N-methylmorpholine and 21.7 g of EEDQ are dissolved in 250 ml of dimethylformamide and stirred overnight at room temperature. The reddish suspension is concentrated by evaporation in a rotary evaporator at 30°, the residue is taken up in 1 liter of ethyl acetate was extracted 4 times with 200 ml of water each time. The dried ethyl acetate phase is concentrated to approximately 100 ml and the product is precipitated by adding 1 liter of ether/petroleum ether (1:1). The supernatant solution is decanted off, the oily material is triturated several times with ether and, while so doing, becomes solid. After crystallisation from ethyl acetate/petroleum ether (1:10), 27 g (79%) of N-tert-butoxycarbonyl-L-seryl-D-isoglutamine-γ-benzyl ester are obtained;
m.p. 83°–85°,
$[\alpha]_D^{20} = -9 \pm 1°$ (c=1, methanol),
$R_f = 0.14$ (chloroform/isopropanol/acetic acid 70:8:2),
$R_f = 0.90$ (ethyl acetate/n-butanol/pyridine/acetic acid/water 42:21:21:6:10).

Benzyloxycarbonyl-D-seryl-D-isoglutamine-γ-tert-butyl ester is obtained in 70% yield, in an analogous manner, from benzyloxycarbonyl-D-serine and D-isoglutamine-γ-tert-butyl ester;
m.p. 126°–128°,
$[\alpha]_D^{20} = -7 \pm 1°$ (c=2, acetic acid),
$R_f = 0.59$ (chloroform/methanol/water 70:30:5),
$R_f = 0.17$ (chloroform/isopropanol/acetic acid 70:8:2).

10.0 g (23.6 mmol) of tert-butoxycarbonyl-L-seryl-D-isoglutamine-γ-benzyl ester are dissolved in 60 ml of absolute pyridine, and 11.0 g (30.7 mmol) of behenic acid chloride in 50 ml of absolute 1,2-dimethoxyethane are added at room temperature. When the reaction is complete (1 hour), 50 ml of methanol are added to the reaction solution, the mixture is left to stand for 3 hours and then concentrated by evaporation and, after being taken up in 400 ml of ethyl acetate, is extracted 4 times with 50 ml of water each time. The ethyl acetate phase is dried, concentrated slightly and left to crystallise in the cold overnight. 16.5 g (94%) of O-behenoyl-N-tert-butoxycarbonyl-L-seryl-d-isoglutamine-γ-benzyl ester are obtained;
m.p. 56°–57°,
$[\alpha]_D^{20} = +3 \pm 1°$ (c=0.25, methanol),
$R_f = 0.54$ (chloroform/isopropanol/acetic acid 70:8:2),
$R_f = 0.73$ (n-butanol/acetic acid/water 75:7.5:21).

11.0 g (14.7 mmol) of O-behenoyl-N-tert-butoxycarbonyl-L-seryl-D-isoglutamine-γ-benzyl ester are suspended in 50 ml of absolute ethyl acetate, and 100 ml of 2 N HCl in ethyl acetate are added at 0° with the exclusion of moisture. The mixture is stirred for 1 hour at 0° and the solvent is evaporated off at 25°. The oily residue is triturated several times with petroleum ether, the supernatant solution is decanted and the pulverulent residue is dried at a high temperature over soda-asbestos (Merck). 9.3 g (93%) of L-(O-behenoyl)-seryl-D-isoglutamine-γ-benzyl ester hydrochloride are obtained as a strongly hydroscopic powder;
$[\alpha]_D^{20} = +3 \pm 1°$ (c=1.1, methanol),
$R_f = 0.43$ (n-butanol/acetic acid/water 75:7.5:21),
$R_f = 0.68$ (ethyl acetate/n-butanol/pyridine/acetic acid/water 42:21:21:6:10).

EXAMPLE 7

1.922 g (2 mmol) of N-acetyl-4,6-O-isopropylideneisomuramyl-L-(O-behenoyl)-seryl-D-isoglutamine-γ-benzyl ester is dissolved in 40 ml of 60% acetic acid and the solution is left to stand at room temperature for 16 hours. 2.0 g of a palladium-on-barium sulphate catalyst (10%) are added and the whole is treated with hydrogen. After 1 hour, the catalyst is filtered off, and the reaction solution is diluted with acetic acid and lyophilised. The residue is dissolved in 60 ml of tert-butanol/water 95:5, the solution is filtered through a PTFE millipore filter (0.2μ) and lyophilised. N-acetyl-isomuramyl-L-(O-behenoyl)-seryl-D-isoglutamine is obtained as a loose powder;
$R_f = 0.53$ (chloroform/methanol/water 70:30:5),
$R_f = 0.64$ (ethyl acetate/n-butanol/pyridine/acetic acid/water 42:21:21:6:10).

The starting material is obtained as follows:
0.65 g (3.17 mmol) of dicyclohexylcarbodiimide is added to 1.05 g (2.6 mmol) of the sodium salt of N-acetyl-4,6-isopropylidene-isomuramic acid, 1.80 g (2.6 mmol) of L-(O-behenoyl)-seryl-D-isoglutamine-γ-benzyl ester hydrochloride and 0.60 g (5.2 mmol) of N-hydroxysuccinimide in 22 ml of dimethylformamide and the whole is stirred for 16 hours at room temperature. The suspension is diluted with 80 ml of ethyl acetate and the filtrate is evaporated to dryness at 30°. The oily residue is chromatographed over silica gel (1:30) in chloroform/methanol 9:1. The fractions that are uniform according to thin-layer chromatography are collected. N-acetyl-4,6-O-isopropylidene isomuramyl-L-(O-behenoyl)-seryl-D-isoglutamine-γ-benzyl ester is obtained;
$R_f = 0.46$ (chloroform/methanol 9:1).

N-acetyl-muramyl-L-(O-behenoyl)-seryl-D-isoglutamine is obtained in an analogous manner;
$[\alpha]_D^{20} = +29 \pm 1°$ (c=0.115, water),
$R_f = 0.82$ (ethyl acetate/n-butanol/pyridine/acetic acid/water 42:21:21:6:10),
$R_f = 0.23$ (chloroform/methanol/water 70:30:5).

The starting materials are obtained as follows:
10 g (21 mmol) of the sodium salt of N-acetyl-1α-O-benzyl-4,6-O-isopropylidene-isomuramic acid (containing NaCl) are dissolved in 100 ml of a mixture of 1,2-dimethoxyethane/water 2:1 and treated with hydrogen in the presence of 5 g of palladium-on-carbon (10%) for 50 hours. The catalyst is filtered off, the filtrate is concentrated by evaporation and the residue is dried over phosphorus pentoxide. 8.1 g of a colourless powder are obtained containing 2.09 mmol of the sodium salt of N-acetyl-4,6-O-isopropylidene-isomuramic acid per gram (containing NaCl);
$R_f = 0.67$ (ethyl acetate/n-butanol/pyridine/acetic acid water 42:21:21:6:10),
$R_f = 0.25$ (chloroform/methanol/water 70:30:5).

The sodium salt of N-acetyl-4,6-O-isopropylidene-muramic acid is obtained analogously from the sodium salt of N-acetyl-1α-O-benzyl-4,6-O-isopropylidene-muramic acid;
$R_f = 0.60$ (ethyl acetate/n-butanol/pyridine/acetic acid/water 42:21:21:6:10),
$R_f = 0.32$ (chloroform/methanol/water 70:30:5), and finally the sodium salt of N-acetyl-4,6-O-isopropylidene-normuramic acid (containing NaCl) is obtained analogously from the sodium salt of N-acetyl-1α-O-benzyl-4,6-O-isopropylidene-normuramic acid;

$R_f$=0.48 (ethyl acetate/n-butanol/pyridine/acetic acid/water 42:21:21:6:10), $R_f$=0.22 (chloroform/methanol/water 70:30:5).

The sodium salt of N-acetyl-1α-O-benzyl-4,6-O-isopropylidene-isomuramic acid is obtained in the following manner:

14.6 g (32.4 mmol) of N-acetyl-1α-O-benzyl-4,6-O-isopropylidene-isomuramic acid ethyl ester are dissolved in 150 ml of methanol, 24.3 ml of 2 N sodium hydroxide solution are added and the mixture is left to stand for one hour at room temperature. After the addition of 8.1 ml of 2 N hydrochloric acid, the reaction solution is concentrated by evaporation and the residue is dried over phosphorus pentoxide. 15.53 g of a colourless powder are obtained containing 2.09 mmol of the sodium salt of N-acetyl-1α-O-benzyl-4,6-O-isopropylidene-isomuramic acid per gram (containing NaCl);

$R_f$=0.54 (chloroform/methanol/acetic acid 85:13:1.5:0.5), $R_f$=0.6 (chloroform/methanol 85:15).

EXAMPLE 8

3.02 g (5 mmol) of N-acetyl-4,6-O-isopropylidenemuramyl-D-seryl-D-isoglutamine-γ-tert-butyl ester are reacted in the usual manner with 1.25 equivalents of oleic acid chloride (Fluka) in pyridine. After leaving the mixture to stand for 30 hours at room temperature, 50 ml of methanol are added and the whole is stirred for 2 hours and then concentrated by evaporation at 30°. The by-products are removed from the residue over a column containing 100 g of UPC$_{12}$ silica gel (charged 4 times; ANTEC) with chloroform, and the product is eluted with chloroform/methanol 95:5 (2.2 g).

1.1 g of the material contained in fractions 22 to 50 is dissolved, in the cold, in 8 ml of 95% trifluoroacetic acid and, after standing for 2 hours at 0°, the solution is concentrated by evaporation; the residue is taken up in 20 ml of tert-butanol and lyophilised. The crude product is purified as before over 100 g of UPC$_{12}$ silica gel in the system chloroform/isopropanol/acetic acid 70:8:2 (10 ml fractions). The N-acetyl-muramyl-D-(O-oleoyl)-seryl-D-isoglutamine contained in fractions 21–60 is taken up in 95% tert-butanol, is filtered through a PTFE millipore filter (0.2μ) and lyophilised;

$[\alpha]_D^{20}$= +26±1° (c=0.395, methanol), $R_f$=0.22 (chloroform/methanol/water 70:30:5), $R_f$=0.62 (acetonitrile/water 3:1).

The starting material is obtained as follows:

5.08 g (12.3 mmol) of benzyloxycarbonyl-D-seryl-D-isoglutamine-γ-tert-butyl ester, dissolved in 300 ml of methanol, are treated with hydrogen for 30 minutes in the presence of 1 g of a palladium-on-carbon catalyst (10%), while the pH is maintained at 3.5 by the addition of methanolic hydrochloric acid (~0.7 N). The foam produced after customary working up and drying over soda-asbestos (Merck) is dissolved in 40 ml of dimethylformamide, 4.24 g (2.3 mmol) of the sodium salt of N-acetyl-4,6-O-isopropylidene-muramic acid (2.9 mmol/g) and 3.34 g (13.5 mmol) of EEDQ are added, and the mixture is stirred overnight at room temperature. The suspension is concentrated by evaporation at 30° and the residue is partitioned between 300 ml of ethyl acetate and 50 ml of saturated potassium chloride solution. The aqueous phase is decanted and the organic phase is extracted three more times using 50 ml of saturated potassium chloride solution each time. The ethyl acetate phase is dried, concentrated to approximately 30 ml and is caused to crystallize by adding, in portions, 150 ml of ether. 5.4 g (73%) of N-acetyl-4,6-O-isopropylidene-muramyl-D-seryl-D-isoglutamine-γ-tert-butyl ester are obtained;

$[\alpha]_D^{20}$= +29° (c=0.782, methanol), $R_f$=0.40 (chloroform/methanol/water 70:30:5), $R_f$=0.60 (acetonitrile/water 3:1).

EXAMPLE 9

0.48 g (4.72 mmol) of acetic anhydride, dissolved in 15 ml of pyridine, is added dropwise to a solution of 1.4 g (1.43 mmol) of N-acetyl-normuramyl-L-(O-behenoyl)-seryl-D-isoglutamine-γ-diphenylmethyl ester in 15 ml of absolute pyridine and the whole is left to stand for 1 hour at room temperature. 1 ml of water is added and, after 15 minutes, the solvent is evaporated off. The residue is taken up in 60 ml of ethyl acetate, the ethyl acetate phase is extracted 5 times with 20 ml of water each time and dried. The residue (1.4 g) remaining after evaporation of the solvent is dissolved in 20 ml of 1,2-dimethoxyethane/water 95:5 and treated with hydrogen for 30 minutes in the presence of palladium-on-barium sulphate (10%). The catalyst is filtered off, the filtrate is concentrated by evaporation and the residue is lyophilised from tert-butanol/water 9:1. The solid material is triturated several times with ether, dissolved again in 20 ml of tert-butanol/water 9:1, filtered through a PTFE millipore filter (0.2μ) and lyophilised. 1.1 g of N-acetyl-1,4,6-O-triacetyl-normuramyl-L-(O-behenoyl)-seryl-D-isoglutamine remains;

$[\alpha]_D^{20}$= +33±1° (c=0.53, methanol), $R_f$=0.38 (chloroform/methanol/water 70:30:5), $R_f$=0.77 (ethyl acetate/n-butanol/pyridine/acetic acid/water 42:21:21:6:10).

The starting material is obtained as follows:

1.5 g (1.84 mmol) of N-acetyl-normuramyl-L-(O-behenoyl)-seryl-D-isoglutamine are dissolved in 40 ml of methanol/1,2-dimethoxyethane 2:1, and 0.7 g (3.7 mmol) of diphenyl-diazomethane are added and the mixture is stirred for 3 hours at room temperature. The red suspension is concentrated by evaporation at 30°, the oily residue is triturated with 200 ml of ether/petroleum ether 1:2 and the insoluble material is filtered off. The precipitate is washed until colourless, is dissolved in 50 ml of methanol and caused to crystallise by adding ether. After filtration, washing and drying, 1.6 g (89%) of N-acetyl-normuramyl-L-(O-behenoyl)-seryl-D-isoglutamine-γ-diphenylmethyl ester remains in the form of colourless crystals;

m.p. 165° with decomposition, $R_f$=0.5 (chloroform/methanol/water 70:30:5).

N-acetyl-1,4,6-triacetyl-normuramyl-L-(O-acetyl)-seryl-D-isoglutamine is obtained analogously from N-acetyl-normuramyl-L-seryl-D-isoglutamine-γ-diphenylmethyl ester.

EXAMPLE 10

0.89 (1 mmol) of N-acetyl-4,6-O-isopropylidenemuramyl-L-(S-stearoyl)-cysteinyl-D-isoglutamine-tert-butyl ester is dissolved in the cold in 10 ml of 95% trifluoroacetic acid. After leaving the solution to stand for 2 hours at 0° it is carefully concentrated, and tert-butanol is added to the residue and then evaporated off (twice). The residue is taken up in tert-butanol/water 95:5, filtered through a Teflon millipore filter (0.2μ) and lyophilised. N-acetyl-muramyl-L-(S-stearoyl)-cysteinyl-D-isoglutamine is obtained as a colourless powder.

The starting material is obtained as follows:

0.526 g (1.65 mmol) of mercuric acetate (Merck) is added to 1.29 g (1.5 mmol) of N-acetyl-4,6-O-isopropylidene-muramyl-L-(S-trityl)-cysteinyl-D-isoglutamine-γ-tert-butyl ester dissolved in a mixture of 10 of ethyl acetate and 5 ml of methanol. After stirring the mixture for 4 hours at room temperature, the mercaptide is decomposed by introducing hydrogen sulphide for 10 minutes. The flocculent, readily filtered mercury sulphide is filtered with suction, the filtrate is concentrated by evaporation and, after dissolving in absolute pyridine, the mercapto group is acylated in the usual manner with 1.1 equivalent of stearic acid chloride. The crude product is purified by chromatography over silica gel. N-acetyl-4,6-O-isopropylidene-muramyl-L-(S-stearoyl)-cysteinyl-D-isoglutamine-tert-butyl ester is obtained.

The completely protected product is obtained in the following manner:

1.74 g (2.2 mmol) of N,S-ditrityl-L-cysteinyl-D-isoglutamine-γ-tert-butyl ester is dissolved in 35 ml of 90% trifluoroethanol and the whole is titrated at room temperature with 0.1 N HCl in 90% trifluoroethanol to pH 3.5 (pH-stat) (19.8 ml used). The thin suspension is diluted with ethyl acetate and tert-butanol and concentrated to a great extent at 30° in vacuo. After adding and evaporating tert-butanol twice, the mixture is taken up in tert-butanol again and lyophilised;

$R_f$=0.66 (acetonitrile/water 3:1).

The crude product obtained above is taken up in 6 ml of dimethylformamide, and 0.78 g (2.2 mmol) of the sodium salt of N-acetyl-4,6-O-isopropylidene-muramic acid, 0.544 g (2.64 mmol) of dicyclohexylcarbodiimide and 0.506 g (4.4 mmol) of N-hydroxysuccinimide are added. Rinsing is carried with 2 ml of acetonitrile and the whole is stirred for 20 hours at room temperature. The suspension is diluted with 4-times its volume of ethyl acetate, the insoluble material is filtered off and the filtrate is evaporated to dryness at 30°. The crude product is freed of the main impurities over silica gel (1:50) in the system chloroform/isopropanol 95:5 (10 ml fractions) and eluted with chloroform/isopropanol 85:15. 1.35 g of 4,6-O-isopropylidene-N-acetyl-muramyl-L-(S-trityl)-cysteinyl-D-isoglutamine-γ-tert-butyl ester is obtained;

$R_f$=0.57 (acetonitrile/water 3:1),
$R_f$=0.69 (chloroform/methanol/water 70:30:5).

The protected dipeptide derivative is obtained in the following manner:

10.54 g (15 mmol) of N,S-ditrityl-L-cysteine-succinimide ester are added to 3.03 g (15 mmol) of D-isoglutamine-γ-tert-butyl ester dissolved in a mixture of 27 ml of dimethylformamide and 3 ml of acetonitrile, and the whole is left to stand for 29 hours at room temperature. The yellowish solution is diluted with 300 ml of ethyl acetate and extracted 10 times using 30 ml of water each time. The organic phase is dried and the solvent is evaporated. The colourless residue is dissolved in 35 ml of hot acetone, and to this there is added 1 ml of methanol and, while stirring, 5 ml of water. The product precipitates on cooling in the form of tufts of colourless needles. 9.7 g (82%) of N,S-ditrityl-L-cysteinyl-D-isoglutamine-γ-tert-butyl ester are obtained;

decomposition range 206°–207°,
$[\alpha]_D^{20}$= +58±1° (c=1.275, chloroform),
$R_f$=0.78 (acetonitrile/water 3:1),
$R_f$=0.65 (chloroform/isopropanol/acetic acid 70:8:2).

EXAMPLE 11

1.09 g (1 mmol) of N-benzyloxycarbonyl-1α-O-benzyl-4,6-O-isopropylidene-normuramyl-L-(O-behenoyl)-seryl-D-isoglutamine-tert-butyl ester is hydrogenated for approximately 1 hour, at room temperature and normal pressure, while maintaining a pH of 7, with 0.5 g of palladium-on-barium sulphate (10%) in 10 ml of 5% aqueous dioxan. The catalyst is filtered off and the free amino group of the normuramic acid is acetylated with the addition of 0.3 ml of acetic anhydride and 6 ml of 5% NaHCO₃ solution. After 2 hours at room temperature, the solution is concentrated in vacuo, and 20 ml of 2 N HCl in ethyl acetate are added to the residue. After stirring for 1 hour at room temperature, the resulting amorphous N-acetyl-1α-O-benzyl-normuramyl-L-(O-behenoyl)-seryl-D-isoglutamine is precipitated with 50 ml of ether;

$R_f$=0.43 (CHCl₃/methanol/H₂O 70:30:5). This compound is hydrogenated for 60 hours with 0.5 g of Pd-on-BaSO₄ in 15 ml of 5% aqueous dioxan.

After filtering off the catalyst, the residue is evaporated to dryness in vacuo and chromatographed over silica gel (Merck) in CHCl₃/methanol 7:3, and the pure fractions are desalted with Dowex-50 H⁺ in dimethoxyethane/H₂O 1:1. After concentration by evaporation, dissolution in tert-butanol, filtration through a millipore filter (0.2μ) and freeze-drying of the filrate, N-acetyl-normuramyl-L-(O-behenoyl)-seryl-D-isoglutamine is obtained as a colourless, amorphous powder;

$R_f$=0.23 (chloroform/methanol/water (70:30:5),
$R_f$=0.59 (acetonitrile/water 3:1),
$R_f$=0.39 (ethyl acetate/n-butanol-pyridine/glacial acetic acid/water 42:21:21:6:10).

The starting material is obtained as follows:

1.0 g (2 mmol) of the sodium salt of N-benzyloxycarbonyl-1α-O-benzyl-4,6-O-isopropylidene-normuramic acid is condensed, analogously to Example 7, with 1.3 g (2 mmol) of L-(O-behenoyl)-seryl-D-isoglutamine-γ-tert-butyl ester hydrochloride, 0.6 g of N-hydroxysuccinimide and 0.65 g of dicyclohexylcarbodiimide in 25 ml of absolute dimethylformamide. After 24 hours at room temperature, the dicyclohexylurea is filtered off with suction, the filrate is evaporated to dryness in an oil vacuum and the residue is chromatographed over silica gel Merck with CHCl₃/methanol 9:1. In this manner, N-benzyloxycarbonyl-1α-O-benzyl-4,6-O-isopropylidene-normuramyl-L-(O-behenoyl)-seryl-D-isoglutamine-γ-tert-butyl ester is obtained;

$[\alpha]_D^{20}$= +75° (c=1, dimethylformamide),
$R_f$=0.55 (CHCl₃/methanol 9:1).

EXAMPLE 12

3.5 g (3.85 mmol) of N-acetyl-1α-O-benzyl-4,6-O-isopropylidene-normuramyl-L-(O-behenoyl)-serine-benzyl ester, dissolved in 50 ml of 1,2-dimethoxyethane/water 95:5, are treated with hydrogen, after the addition of 2 g of Pd-on-barium sulphate catalyst, for 3 hours. The residue remaining after concentration by evaporation and drying is dissolved in 12 ml of dimethylformamide/chloroform 3:1. There are then added, in the cold, 0.78 g (3.85 mmol) of D-isoglutamine-γ-tert-butyl ester, 0.531 g (4.63 mmol) of N-hydroxysuccinimide and, finally, 0.952 g (4.62 mmol) of dicyclohexylcarbodiimide, and the whole is stirred for 24 hours at room temperature. 0.5 ml of acetic acid are added to the suspension which, after 30 minutes, is diluted with 60 ml of ethyl acetate, and the precipitate is filtered with suction. The filtrate is worked up analogously to Example 2 and the crude product is additionally purified over silica gel (1:30) in the system chloroform/isopropanol 95:5. 2.6 g of N-acetyl-1α-O-benzyl-4,6-O-isopropylidene-normuramyl-L-(O-behenoyl)-seryl-D-isoglutamine-γ-tert-butyl ester are obtained;

$R_f$=0.85 (chloroform/methanol/water 70:30:5)
$R_f$=0.43 (chloroform/isopropanol/acetic acid 70:8:2).

The starting material is obtained as follows:

3.52 g (6 mmol) of N-acetyl-1α-O-benzyl-4,6-O-isopropylidene-normuramyl-L-serine-benzyl ester are acylated, analogously to Example 2, with behenic acid chloride in absolute pyridine. 3.93 g (72%) of N-acetyl-1α-O-benzyl-4,6-O-isopropylidene-normuramyl-L-(O-behenoyl)-serinebenzyl ester are obtained;

$R_f$=0.85 (acetonitrile/water 3:1),
$R_f$=0.35 (ethyl acetate).

The starting compound is obtained as follows:

4.24 g (12.3 mmol) of the sodium salt of N-acetyl-1α-O-benzyl-4,6-O-isopropylidene-normuramic acid, 2.85 g (12.3 mmol) of L-serine-benzyl ester hydrochloride and 3.34 g (13.5 mmol) of EEDQ in dimethylformamide are reacted analogously to Example 8. The solvent is removed in vacuo, the residue is taken up in 150 ml of ethyl acetate and, in the cold, is extracted first with 15 ml each time of water (twice), then with cold 1 N HCl (4 times), saturated sodium bicarbonate solution and again water (twice). After evaporation of the solvent, 5 g (70%) of N-acetyl-1α-O-benzyl-4,6-O-isopropylidene-normuramyl-L-serine-benzyl ester are obtained as a colourless foam;

$[\alpha]_D^{20}$= +75° (c=1, chloroform),
$R_f$=0.6 (chloroform/methanol 15:1),
$R_f$=0.5 (ethyl acetate).

EXAMPLE 13

2-Acetamino-2-deoxy-3-O-(D-2-propionyl-L-[O-behenoyl]-seryl-D-isoglutamine is obtained starting from known 2-acetamino-1α-O-benzyl-2-deoxy-5,6-O-isopropylidene-3-O-(D-1-carboxyethyl)-D-mannofuranoside [Agric. Biol. Chem. 42, 2187 (1978)] by coupling with a peptide analogously to Example 6 and splitting off the protecting groups in the usual manner.

EXAMPLE 14

N-benzyloxycarbonyl-1α-O-benzyl-muramyl-L-O-benzoyl-seryl-D-isoglutamine-benzyl ester is hydrogenated, analogously to Example 7, at pH 7 to produce muramyl-L-O-benzoyl-seryl-D-isoglutamine as an internal salt.

This compound can be converted into corresponding N-acylated muramylpeptides by reacting with a hydroxysuccinimide ester of alkyl- and arylcarboxylic acids with the addition of triethylamine or NaHCO3 solution (see Example 11): There is thus obtained N-(p-chloro-benzoyl)-muramyl-L-(O-behenoyl)-seryl-D-isoglutamine, N-pivaloyl-muramyl-L-(O-behenoyl)-seryl-D-isoglutamine and N-octanoyl-muramyl-L-(O-behenoyl)-seryl-D-isoglutamine.

EXAMPLE 15

Analogously to Example 5, 2-(1,2,5,6-diisopropylidene-glucofuranosyl-3-O)-D-propionic acid (Carbohydrate Research 79, C 17 [1980]) is coupled with a peptide, and the protecting groups are split off with a dilute acid and by catalytic hydrogenation, to produce glucopyranosyl-3-O-D-propionyl-L-(O-dodecyloxycarbonyl)-seryl-D-isoglutamine.

Galactopyranosyl-3-O-D-propionyl-L-(O-dodecyloxycarbonyl)-seryl-D-isoglutamine is obtained analogously from 2-(1,2,5,6-diisopropylidene-galactofuranosyl-3-O)-D-propionic acid.

EXAMPLE 16

N-acetyl-1,4,6-O-tris-trimethylsilyl-normuramyl-L-(O-behenoyl)-seryl-D-isoglutamine-trimethylsilyl ester is obtained from N-acetyl-normuramyl-L-(O-behenoyl)-seryl-D-isoglutamine with N,O-bis-trimethylsilyl carbamate in absolute dimethylformamide at room temperature.

EXAMPLE 17

N-acetyl-1,4,6-O-triacetyl-muramyl-L-(N-methyl-O-behenoyl)-seryl-D-isoglutamine is obtained analogously to Example 9.

EXAMPLE 18

The azido group in 1-O-benzyl-2-acetylamino-6-azido-2,6-dideoxy-3-O-(D-1-methoxycarbonyl-ethyl)-α-D-glucopyranoside

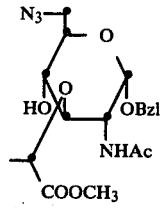

is reduced to the amino group, is acetylated and, after hydrolysis of the methyl ester, is linked, analogously to Example 7, with L-seryl-D-isoglutamine-γ-tert-butyl ester. After acylation of the hydroxy group of serine and removal of the protecting groups, N-acetyl-6-acetylamino-6-deoxy-muramyl-L-(O-dodecanoyl)-D-isoglutamine is obtained.

EXAMPLE 19

2-Acetylamino-1α-O-benzyl-2-deoxy-4,6-O-isopropylidene-O-glucose is etherified with α-bromoisobutyric acid methyl ester. After hydrolysis of the ester, coupling of L-seryl-D-isoglutamine-γ-benzyl ester hydrochloride and acylation with stearic acid chloride and splitting off of the protecting groups, 2-acetylamino-2-deoxy-3-O-(1,1-dimethyl-acetyl-L-O-stearoyl-seryl-D-isoglutamine)-D-glucose is obtained.

EXAMPLE 20

The sodium salt of N-acetyl-4,6-O-isopropylidene-muramic acid is coupled, analogously to Example 7, with L-(O-behenoyl)-seryl-D-γ-carboxyglutamic acid γ,γ-di-tert-butyl ester α-glycinamide. After removing the protecting groups, N-acetyl-muramyl-L-(O-behenoyl)-seryl-D-γ-carboxyglutamyl-glycinamide is obtained.

EXAMPLE 21

N-Acetyl-normuramyl-L-(O-palmitoyl)-α-methyl-seryl D-isoglutamine is obtained, analogously to Example 7, from the sodium salt of N-acetyl-1α-O-benzyl-4,6-

O-isopropylidene-normuramic acid and L-(O-palmitoyl)-α-methyl-seryl-D-isoglutamine-γ-tert-butyl ester after splitting off the protecting groups.

EXAMPLE 22

The N-acetyl-1α-O-benzyl-4,6-O-isopropylidene-normuramyl-L-serine-benzyl ester described in Example 12 is hydrogenated and linked, analogously to Example 12, with the following derivatives: D-γ-carboxy-glutamic acid γ,γ-dimethyl ester α-amide and D-γ-carboxy-glutamic acid γ'-methyl ester α,γ-diamide.

After acylation of the β-hydroxy group of serine and removal of the protecting groups, N-acetyl-normuramyl-L-(O-behenoyl)-seryl-D-γ-carboxyglutamic acid γ,γ-dimethyl ester α-amide and N-acetyl-normuramyl-L-(O-behenoyl)-seryl-D-γ-carboxyglutamic acid γ-methyl ester α,γ-diamide, respectively, are obtained.

EXAMPLE 23

Manufacture of 1000 capsules each containing 260 mg of the active ingredients:

| Composition: | |
|---|---|
| Rifampicin | 250 g |
| N—acetyl-normuramyl-L-O—behenoyl-seryl-D-isoglutamine | 10 g |
| talc | 36 g |
| wheat starch | 24 g |
| magnesium stearate | 16 g |
| lactose | 4 g |
| | 340 g |

Preparation

The pulverulent substances are forced through a sieve having a mesh width of 0.6 mm and mixed thoroughly. Gelatine capsules are each filled with 340 g of this mixture using a capsule-filling machine.

EXAMPLE 24

N-acetyl-muramyl-L-(O-behenoyl)-4-hydroxyprolyl-D-isoglutaminyl-L-alanine is obtained, analogously to Example 7, from the sodium salt of N-acetyl-4,6-O-isopropylidene-muramic acid and L-O-behenoyl-4-hydroxyprolyl-D-isoglutaminyl-L-alanine-benzyl ester hydrochloride after splitting off the protecting groups in the usual manner.

EXAMPLE 25

The sodium salt of N-acetyl-4,6-O-isopropylidene-muramic acid and N$^\epsilon$-tert-butoxycarbonyl-L-lysyl-D-glutamic acid dimethyl ester hydrochloride are linked analogously to Example 7. After splitting off the protecting groups by acidolysis and acylating with palmitic acid N-hydroxy-succinimide ester, N-acetyl-muramyl-L-(N$^\epsilon$-palmitoyl)-lysyl-D-glutamic acid dimethyl ester is obtained.

We claim:

1. Derivatives of pyranoses of the formula I,

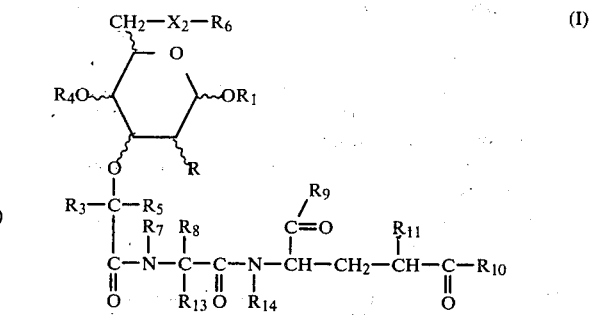

in which

R represents hydroxy, amino or a radical of the formula

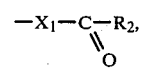

$X_1$ and $X_2$, independently of one another, each represents $NR_{15}$ or an oxygen atom, wherein $R_{15}$ represents hydrogen or lower alkyl, $R_1$ and $R_4$, independently of one another, each represents hydrogen or acyl or a hydroxy-protecting group, $R_6$ represents hydrogen, acyl or, if $X_2$ represents an oxygen atom, a hydroxy-protecting group, $R_2$ represents alkyl or alkoxy, each of which is unsubstituted or substituted by free, etherified or esterified hydroxy or mercapto, oxo, amino or acylamino, or represents phenyl-lower alkoxy or phenyl, each of which is unsubstituted or substituted, substitutents of the phenyl-moiety being lower alkyl or free, etherified or esterified hydroxy, and substituents of the alkoxy-moiety being free, etherified or esterified hydroxy, $R_3$, $R_5$, $R_7$, $R_{13}$ and $R_{14}$, independently of one another, each represents hydrogen or lower alkyl, and $R_8$ represents a lower alkyl or phenyl-lower alkyl radical, which may also be bonded to $R_7$ and which carries an oxycarbonyl, mercaptocarbonyl or aminocarbonyl group which is bonded to an aliphatic, cycloaliphaticaliphatic, cycloaliphatic or aromatic radical $R_o$ which may be interrupted by oxycarbonyl, mercaptocarbonyl and/or iminocarbonyl and has more than 6 and up to 90 carbon atoms, $R_9$ and $R_{10}$ each represent optionally etherified hydroxy or amino which is unsubstituted or substituted by lower alkyl which is unsubstituted or substituted by free, etherified or esterified hydroxy or mercapto or by free, esterified or amidated carboxy, and $R_{11}$ represents hydrogen or a radical of the formula —C(=O)—$R_{12}$ (Ia), in which $R_{12}$ represents optionally etherified hydroxy or amino which is unsubstituted or substituted by lower alkyl which is unsubstituted or substituted by free, etherified or esterified hydroxy or mercapto or by free, esterified or amidated carboxy, and salts of compounds of the formula I having at least one salt-forming group.

2. Compounds according to claim 1, the pyranose moiety of which is derived from D-glucose.

3. Compounds according to claim 1, the pyranose moiety of which is derived from D-mannose or D-galactose.

4. Compounds of the formula I, according to claim 1, which in the case of asymmetrical substitution have the (D)-configuration at the C-$NR_{14}$.

5. Compounds of the formula I, according to claim 4, which in the case of asymmetrical substitution have the (D)-configuration at the C-$R_3$ and the (L)-configuration at the C-$R_8$.

6. Compounds of the formula I, according to claim 1, in which R represents a radical of the formula

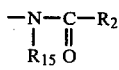

and $X_2$ represents an oxygen atom.

7. Compounds of the formula I, according to claim 1, in which $R_5$, $R_{13}$, $R_{14}$ and $R_{15}$ each represents hydrogen.

8. Compounds of the formula I, according to claim 1 in which $R_1$, $R_4$ and $R_6$ each represents hydrogen, optionally unsaturated alkanoyl having from 2 to 25 carbon atoms, or benzoyl which is unsubstituted or substituted by lower alkyl of free, etherified or esterified hydroxy.

9. Compounds of the formula I, according to claim 1, in which $R_6$ represents the radical $R_oC=O$, wherein $R_o$ has the meaning given in claim 1.

10. Peptide derivatives, according to claim 1, of glucosamine compounds of the formula

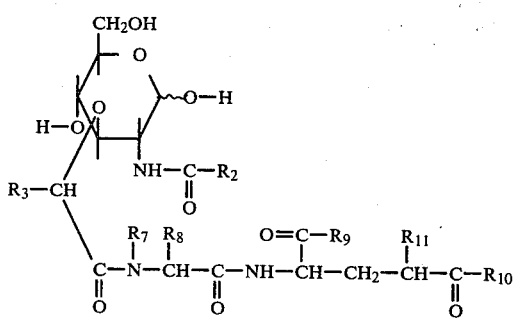

in which $R_2$ represents lower alkyl, phenyl, lower alkoxy or phenyl-lower alkoxy, each of which is unsubstituted or substituted, substituents of lower alkyl and lower alkoxy being free, etherified or esterified hydroxy or mercapto, or oxo, amino or acylamino, and substituents of phenyl or phenyl-lower alkoxy being in the phenyl moiety lower alkyl or free, etherified or esterified hydroxy and in the alkoxy-moiety free, etherified or esterified hydroxy, $R_3$ represents hydrogen or lower alkyl, $R_7$ represents hydrogen or lower alkyl, and $R_8$ represents a lower alkyl or phenyl-lower alkyl radical, which may also be bonded to $R_7$ and which carries an oxycarbonyl, mercaptocarbonyl or aminocarbonyl group which is bonded to a long-chain aliphatic or cycloaliphatic hydrocarbon radical, each of which is unsubstituted or substituted by free, etherified or esterified hydroxy, or mercapto, or by oxo, amino or acylamino, it being possible for an aliphatic hydrocarbon radical to be substituted by a cycloaliphatic hydrocarbon radical and/or to be interrupted by oxycarbonyl, mercaptocarbonyl and/or iminocarbonyl, $R_9$ and $R_{10}$ each represents optionally etherified hydroxy or amino which is unsubstituted or substituted by lower alkyl which is unsubstituted or substituted by free, etherified or esterified hydroxy or mercapto or by free, esterified or amidated carboxy, and $R_{11}$ represents hydrogen or a radical of the formula —C(=O)—$R_{12}$ (Ia), in which $R_{12}$ represents optionally etherified hydroxy or amino which is unsubstituted or substituted by lower alkyl which is unsubstituted or substituted by free, etherified or esterified, hydroxy or mercapto or by free, esterified or amidated carboxy, and salts of compounds of the formula Ic having at least one salt-forming group.

11. Compounds of the formula Ic, according to claim 10, characterized in that the radical of the hydroxyacetic acid with the grouping of the formula —CH($R_3$)— in which $R_3$ represents lower alkyl is in the D-form, the radical of the aminoacetic acid with the grouping of the formula —CH($R_8$)— is in the L-form and the radical of the terminal α-aminoglutaric acid compound is in the D-form, or salts of such compounds having salt forming groups.

12. Compounds of the formula Ic, according to claim 10, in which $R_2$ represents lower alkyl or lower alkoxy each optionally substituted by hydroxy, lower alkoxy, lower alkanoyloxy or halogen, or phenyl or phenyl-lower alkoxy each optionally substituted by lower alkyl, hydroxy, lower alkoxy, lower alkanoyloxy or halogen, $R_3$ represents hydrogen or lower alkyl, $R_7$ represents hydrogen or lower alkyl, and $R_8$ represents a lower alkyl or phenyl-lower alkyl radical which carries as substituent an oxycarbonyl, mercaptocarbonyl or aminocarbonyl group, which is itself in turn bonded to an alkyl or alkenyl radical having more than 6 and up to 90 carbon atoms optionally substituted by hydroxy, lower alkoxy, lower alkanoyloxy, oxo or halogen, or to a cycloaliphatically substituted alkyl or alkenyl radical having up to 30 carbon atoms, and in which the alkyl, alkenyl and cycloaliphatically substituted alkyl or alkenyl radicals may also be interrupted by one or two oxycarbonyl or iminocarbonyl groups, $R_{11}$ represents hydrogen or a radical of the formula Ia, and each of the radicals $R_9$, $R_{10}$ and $R_{12}$ represents hydroxy, lower alkoxy, amino, or amino which is substituted by lower alkyl optionally containing carboxy, lower alkoxycarbonyl or carbamoyl, wherein in such compounds the radical of the hydroxyacetic acid with the grouping of the formula —CH($R_3$)— in which $R_3$ represents lower alkyl is in the D-form, the radical of the aminoacetic acid with the grouping of the formula —CH($R_8$)— is in the L-form, and the radical of the terminal α-aminoglutaric acid compound is in the D-form, and salts of such compounds having salt-forming groups.

13. Compounds of the formula Ic, according to claim 10, in which $R_2$ represents lower alkyl having up to 4 carbon atoms, or phenyl, $R_3$ represents hydrogen or lower alkyl having up to 4 carbon atoms, $R_7$ represents hydrogen and $R_8$ represents a lower alkyl radical having from 1 to 4 carbon atoms or a phenyl-lower alkyl radical, each of which carries as substituent an oxycarbonyl, mercaptocarbonyl or aminocarbonyl group which is itself in turn bonded to alkyl or alkenyl having more than 10 and up to 50 carbon atoms optionally substituted by hydroxy, lower alkoxy, oxo or halogen, or to a tetracyclic cycloalkylalkyl or cycloalkylalkenyl radical having more than 20 and up to 50 carbon atoms optionally substituted by hydroxy, lower alkoxy, oxo or halogen, wherein such radicals may also be interrupted by 1 or 2 oxycarbonyl or iminocarbonyl groups, $R_9$ represents amino, or lower alkylamino optionally containing carboxy or carbamoyl, $R_{10}$ represents hydroxy and $R_{11}$ represents hydrogen, wherein in such compounds the radical of the hydroxyacetic acid with the grouping of the formula —CH($R_3$)— in which $R_3$ represents lower alkyl is in the D-form, the radical of the aminoacetic acid with the grouping of the formula —CH($R_8$)— is in the L-form and the radical of the terminal α-aminoglutaric acid compound is in the D-form, and pharmaceutically acceptable salts of such compounds having salt-forming groups.

14. Compounds of the formula Ic, according to claim 10, in which $R_2$ represents lower alkyl having up to 4 carbon atoms, and phenyl, $R_3$ represents especially hydrogen, and also lower alkyl having up to 4 carbon atoms, $R_7$ represents hydrogen, $R_8$ represents lower alkyl having from 1 to 4 carbon atoms or benzyl, each of which carries as substituent an oxycarbonyl, mercaptocarbonyl or aminocarbonyl group which is preferably bonded via the hetero atom to the lower alkyl or benzyl radical respectively, and which is itself bonded to alkyl or alkenyl having more than 10 and up to 50 carbon atoms optionally substituted by hydroxy, lower alkoxy or oxo, or to a tetracyclic cycloalkylalkyl or cycloalkenylalkyl radical having more than 20 and up to 50 carbon atoms optionally substituted by hydroxy or lower alkoxy, which radicals may also be interrupted by an oxycarbonyl or iminocarbonyl group, $R_9$ represents amino, $R_{10}$ represents hydroxy and $R_{11}$ represents hydrogen, wherein in such compounds the radical of the hydroxyacetic acid with the grouping of the formula —CH($R_3$)— in which $R_3$ represents lower alkyl is in the D-form, the radical of the aminoacetic acid with the grouping of the formula —CH($R_8$)— is in the L-form and the radical of the terminal α-aminoglutaric acid compound is in the D-form, and pharmaceutically acceptable salts of such compounds having salt-forming groups.

15. Compounds of the formula Ic, according to claim 14, in which $R_2$ represents methyl or phenyl and $R_3$ represents hydrogen or methyl, and pharmaceutically acceptable salts of such compounds having salt-forming groups.

16. Compounds of the formula Ic, according to claim 10, in which $R_2$ represents lower alkyl having up to 3 carbon atoms, or phenyl, $R_3$ represents hydrogen or methyl, $R_7$ represents hydrogen, $R_8$ represents lower alkyl having from 1 to 3 carbon atoms, which carries as substituent an oxycarbonyl, mercaptocarbonyl or aminocarbonyl group which is bonded via the hetero atom to the lower alkyl radical and which is itself in turn bonded to alkyl or alkenyl having more than 10 and up to 50 carbon atoms optionally substituted by hydroxy, lower alkoxy or oxo, or to a tetracyclic cycloalkylalkyl or cycloalkenylalkyl radical having more than 20 and up to 50 carbon atoms optionally substituted by hydroxy or lower alkoxy, which radicals may also be interrupted by oxycarbonyl or iminocarbonyl, $R_9$ represents amino, lower alkylamino or carbamoyl-lower alkylamino or hydroxy, $R_{10}$ represents hydroxy, lower alkoxy, amino or carbamoyl-lower alkylamino and $R_{11}$ represents hydrogen, wherein in such compounds the radical of the hydroxyacetic acid with the grouping —CH($R_3$)— in which $R_3$ represents methyl is in the D-form, the radical of the aminoacetic acid with the grouping —CH($R_8$)— is in the L-form and the radical of the terminal α-aminoglutaric acid compound is in the D-form, and pharmaceutically acceptable salts of such compounds having salt-forming groups.

17. Compounds of the formula Ic, according to claim 11, in which $R_2$ represents lower alkyl having up to 3 carbon atoms, $R_3$ represents hydrogen or methyl, $R_7$ represents hydrogen, $R_8$ represents lower alkyl having from 1 to 4 carbon atoms which carries as substituent an oxycarbonyl, mercaptocarbonyl or aminocarbonyl group which is bonded via the hetero atom to the lower alkyl radical and which is itself bonded to alkyl having more than 10 and up to 50 carbon atoms which may also be interrupted by iminocarbonyl, $R_9$ represents amino, hydroxy or lower alkoxy having from 1 to 3 carbon atoms, $R_{10}$ represents hydroxy, lower alkoxy having from 1 to 3 carbon atoms, or amino and $R_{11}$ represents hydrogen or carboxy, and pharmaceutically acceptable salts of such compounds having at least one salt-forming group.

18. Compounds of the formula Ic, according to claim 17, in which $R_8$ represents alkanoyloxymethyl or alkanoyloxy-ethyl having from 10 to 30 carbon atoms, $R_9$ represents amino and $R_{10}$ represents hydroxy, and pharmaceutically acceptable salts thereof.

19. A compound according to claim 11, namely N-acetylnormuramyl-L-O-(N-behenoyl-glycyl)-seryl-D-isoglutamine or a pharmaceutically acceptable salt thereof.

20. A compound according to claim 11, namely N-acetylnormuramyl-L-O-behenoyl-seryl-D-isoglutamine or a pharmaceutically acceptable salt thereof.

21. A compound according to claim 11, namely N-acetylmuramyl-L-O-[N-(D,L-2-n-hexadecanoyl-amino-n-hexadecanoyl)-L-alanyl]-threonyl-D-isoglutamine or a pharmaceutically acceptable salt thereof.

22. A compound according to claim 11, namely N-acetylmuramyl-L-S-stearoyl-cysteinyl-D-isoglutamine or a pharmaceutically acceptable salt thereof.

23. A compound according to claim 11 selected from the group consisting of
N-acetyl-normuramyl-L-O-[N-(12-hydroxy-cis-9-octadecenoyl)-glycyl]-seryl-D-isoglutamine,
N-benzoyl-normuramyl-L-O-stearoyl-seryl-D-isoglutamine,
N-acetyl-muramyl-L-O-(ω-n-stearoylamino-n-undecanoyl)-threonyl-D-isoglutamine,
N-acetyl-muramyl-L-O-[N-(3-hydroxy-etiocholenoyl)-6-amino-hexanoyl]-γ-hydroxyprolyl-D-isoglutamine,
N-acetyl-muramyl-L-O-behenoyl-tyrosyl-D-isoglutamine,
N-acetyl-muramyl-L-($C_\gamma$)-[tetracosylamido-glycyl]-glutamyl-D-isoglutamine,
N-acetyl-muramyl-L-[($C_\gamma$)-lauryl]-glutamyl-D-isoglutamine,
N-acetyl-normuramyl-L-(γ-stearoylamino)-α-aminobutanoyl-D-isoglutamine,
N-acetyl-muramyl-L-(O-behenoyl-N-methyl)-seryl-D-isoglutamine,
N-acetyl-muramyl-L-($N^\epsilon$-palmitoyl)-lysyl-D-glutamic acid dimethyl ester or a pharmaceutically acceptable salt of these compounds having a salt-forming group.

24. A compound according to claim 11, namely N-benzoylnormuramyl-L-(O-stearoyl)-seryl-D-glutamic acid dimethyl ester.

25. A compound according to claim 11, namely N-benzoylnormuramyl-L-(O-behenoyl)-seryl-D-isoglutamine or a pharmaceutically acceptable salt thereof.

26. A compound according to claim 10, namely N-acetylisomuramyl-L-(O-behenoyl)-seryl-D-isoglutamine or a pharmaceutically acceptable salt thereof.

27. A compound according to claim 11, namely N-acetylmuramyl-L-(O-behenoyl)-seryl-D-isoglutamine or a pharmaceutically acceptable salt thereof.

28. A compound according to claim 1 selected from the group consisting of
N-acetyl-muramyl-D-(O-oleoyl)-seryl-D-isoglutamine,
N-acetyl-1,4,6-O-triacetyl-normuramyl-L-(O-behenoyl)-seryl-D-isoglutamine,
N-acetyl-muramyl-L-(4-behenoyloxy)-prolyl-D-isoglutaminyl-L-alanine, and
N-acetyl-muramyl-L-(O-behenoyl)-seryl-D-$\gamma$-carboxy-glutamylglycinamide or a pharmaceutically acceptable salt of these compounds.

29. A pharmaceutical preparation that contains an immunopotentiating effective amount of a pharmacologically active compound of the formula I according to claim 1 or a pharmaceutically acceptable salt of such a compound having a salt-forming group together with a significant amount of a pharmaceutically acceptable carrier.

30. A method for potentiating the immune response of humans and animals which comprises administering an effective amount of a compound of claim 1 or a pharmaceutically acceptable salt of such a compound having a salt-forming group.

31. Pharmaceutical preparations that contain an effective amount of at least one antibiotic and an immunopotentiating effective amount of at least one pyranose derivative of the formula I according to claim 1 and/or a salt of the same together with a significant amount of a pharmaceutically acceptable carrier.

32. Feedstuffs and feedstuff additives that contain an effective amount of at least one antibiotic and an immunopotentiating effective amount of at least one muramyl peptide according to claim 1 and/or a salt of the same together with a significant amount of food or of a pharmaceutically acceptable carrier.

33. Peptides of the formula II

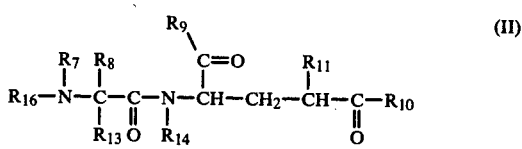

in which $R_{16}$ represents hydrogen or an amino-protecting group or the radical of the formula

represents an activated amino group and the remaining substituents have the meanings given in one of the claims 1, 7, 10, 12–14 and 16, and salts of such compounds having salt-forming groups.

34. Pharmaceutical preparations that contain an immunopotentiating effective amount of the unprotected peptides of the formula II according to claim 33 or of a pharmaceutically acceptable salt of such a peptide together with a significant amount of a pharmaceutically acceptable carrier.

* * * * *